US006716580B2

(12) United States Patent  
Gold et al.

(10) Patent No.: US 6,716,580 B2  
(45) Date of Patent: Apr. 6, 2004

(54) METHOD FOR THE AUTOMATED GENERATION OF NUCLEIC ACID LIGANDS

(75) Inventors: Larry Gold, Boulder, CO (US); Dominic A. Zichi, Boulder, CO (US); Robert D. Jenison, Boulder, CO (US); Daniel J. Schneider, Arvada, CO (US)

(73) Assignee: SomaLogic, Inc., Boulder, CO (US)

( * ) Notice: Subject to any disclaimer, the term of this patent is extended or adjusted under 35 U.S.C. 154(b) by 0 days.

(21) Appl. No.: 09/815,171

(22) Filed: Mar. 22, 2001

(65) Prior Publication Data

US 2002/0064780 A1 May 30, 2002

Related U.S. Application Data

(63) Continuation-in-part of application No. 09/616,284, filed on Jul. 14, 2000, which is a continuation-in-part of application No. 09/356,233, filed on Jul. 16, 1999, which is a continuation-in-part of application No. 09/232,946, filed on Jan. 19, 1999, which is a continuation-in-part of application No. 09/143,190, filed on Aug. 27, 1998, now Pat. No. 6,110,900, which is a continuation-in-part of application No. 08/792,075, filed on Jan. 31, 1997, now Pat. No. 5,861,254, which is a continuation of application No. 08/769,609, filed on Jun. 6, 1995, now Pat. No. 5,843,653, which is a continuation of application No. 07/714,131, filed on Jun. 10, 1991, now Pat. No. 5,475,096, which is a continuation-in-part of application No. 07/536,428, filed on Jun. 11, 1990, now abandoned.

(51) Int. Cl.$^7$ .......................... C12Q 1/68; C12P 19/34; C12M 1/36; C07H 21/04

(52) U.S. Cl. .................... 435/6; 435/91.1; 435/91.2; 435/283.1; 435/287.2; 435/288.3; 536/23.1; 536/24.3; 536/25.4

(58) Field of Search .......................... 435/91.2, 6, 91.1, 435/283.1, 287.2, 288.3; 536/25.4, 24.3, 231; 7530/412

(56) References Cited

U.S. PATENT DOCUMENTS 4,683,195 A 7/1987 Mullis et al.

(List continued on next page.)

FOREIGN PATENT DOCUMENTS

| GB | 2 183 661 | 6/1987 |
|----|-----------|--------|
| WO | WO89/06694 | 7/1989 |
| WO | WO91/19813 | 12/1991 |
| WO | WO92/06380 | 4/1992 |
| WO | WO92/14843 | 9/1992 |
| WO | WO93/05182 | 3/1993 |

OTHER PUBLICATIONS

Cheskis and Freedman (1996) Biochemistry, 35:3309–3318.  
Cox (1998) Colin, Biotechnal. Prog. 14:845–850.

(List continued on next page.)

Primary Examiner—B. J. Forman  
(74) Attorney, Agent, or Firm—Swanson & Bratschun, LLC

(57) ABSTRACT

The present invention includes a method and device for performing automated SELEX. The steps of the SELEX process are performed at one or more work stations on a work surface by a robotic manipulator controlled by a computer. The invention also includes methods and reagents to obviate the need for size-fractionation of amplified candidate nucleic acids before beginning the next round of the SELEX process.

9 Claims, 16 Drawing Sheets

U.S. PATENT DOCUMENTS

| | | | |
|---|---|---|---|
| 5,443,791 | A | 8/1995 | Cathcart et al. |
| 5,475,096 | A | 12/1995 | Gold et al. |
| 5,567,588 | A | 10/1996 | Gold et al. |
| 5,580,737 | A | 12/1996 | Polisky et al. |
| 5,610,287 | A | 3/1997 | Nikiforov et al. |
| 5,620,850 | A | 4/1997 | Bamdad et al. |
| 5,656,493 | A | 8/1997 | Mullis et al. |
| 5,723,323 | A | 3/1998 | Kauffman et al. |
| 5,737,498 | A | 4/1998 | Murray |
| 5,861,254 | A | 1/1999 | Schneider et al. |
| 5,866,336 | A | 2/1999 | Nazarenko et al. |
| 5,955,268 | A * | 9/1999 | Granados et al. |
| 5,985,548 | A | 11/1999 | Collier et al. |
| 6,235,471 | B1 | 5/2001 | Knapp et al. |

OTHER PUBLICATIONS

Ellington and Szostak, (1990) p. 84, Abstract Presented at Cold Spring Harbor RNA Processing Meeting, May 16–20, 1990, Selection of RNAs with Ligand–Specific Binding Activity from Pools of Random Sequence.
Fisher et al., (1994) *Protein Science*, 3:257–266.
Joyce (1989) Gene 82:83.
Joyce and Inoue (1989) Nucleic Acids Research 17:711.
Karlsson (1994) Analytical Biochemistry 221:142–151.
Karlsson (1994) Analytical Biochemistry 221:142–151.
Kinzler and Vogelstein (1989) Nucleic Acids Research 14:3645.
Kramer (1974) J. Mol. Biol. 89:719.
Levisohn and Spiegleman (1969) Proc. Natl. Acad. Sci. USA 63:805–811.
Levisohn and Spiegleman (1968) Proc. Natl. Acad. Sci. USA 60:866–872.
Oliphant et al. (1989) Mol. Cell. Biol. 9:2944.
Oliphant and Struhl (1988) Nucleic Acids Research 16:7673–7683.
Oliphant and Struhl (1987) Methods in Enzymology 155:568–582.
Oliphant et al. (1986) Gene 44:177–183, Nussbaum & Strul.
Robertson and Joyce (1990) Nature 344:467.
Szostak (1988) *Redesigning the Molecules of Life*, (S.A. Benner ed.) Springer–Verlag Berlin Heidelberg, pp. 87–113.
Thiesen and Bach (1990) Nucleic Acids Res. 18:3203.
Crameri & Stemmer (1993) *Nucleic Acids Research 21*:4410.
Hanna (1989) *Methods in Enzymology 180*:383.
Heid, et al. (1996) *Genome Res. 6*:986.
Mitsuhashi, Technical Report: Part 2. Basic Requirements for Designing Optimal PCT Primers. J. of Clinical Lab. Anal. 10(5): 285–293. (1996).

* cited by examiner

SEQUENCE LISTING

<160> NUMBER OF SEQ ID NOS: 32

<210> SEQ ID NO 1
<211> LENGTH: 43
<212> TYPE: DNA
<213> ORGANISM: Artificial Sequence
<220> FEATURE:
<223> OTHER INFORMATION: Description of Artificial Sequence:  Synthetic
      Sequence
<221> NAME/KEY: modified_base
<222> LOCATION: (1)..(43)
<223> OTHER INFORMATION: T at position 10 is substituted with
      DABCYL-(CH2)6-; G at position 1 is substituted
      with 6-FAM

<400> SEQUENCE: 1
gagcgaagct ctaatacgac tcactatagg gaggacgatg cgg                43

<210> SEQ ID NO 2
<211> LENGTH: 51
<212> TYPE: DNA
<213> ORGANISM: Artificial Sequence

```
<220> FEATURE:
<223> OTHER INFORMATION: Description of Artificial Sequence:  Synthetic
      Sequence
<221> NAME/KEY: modified_base
<222> LOCATION: (1)..(51)
<223> OTHER INFORMATION: T at position 10 is substituted with
      DABCYL-(CH2)6-; G at position 1 is substituted
      with 6-FAM

<400> SEQUENCE: 2
gagcgaagct ctaatacgac tcactatagg gagacaagaa taaacgctca a            51

<210> SEQ ID NO 3
<211> LENGTH: 61
<212> TYPE: DNA
<213> ORGANISM: Artificial Sequence
<220> FEATURE:
<223> OTHER INFORMATION: Description of Artificial Sequence:  Synthetic
      Sequence
<221> NAME/KEY: misc_feature
<222> LOCATION: (16)..(45)
<223> OTHER INFORMATION: N at positions 16-45 is A, C, G or T

<400> SEQUENCE: 3
gggaggacga tgcggnnnnn nnnnnnnnnn nnnnnnnnnn nnnnncagac gacgagcggg   60
a                                                                  61

<210> SEQ ID NO 4
<211> LENGTH: 23
<212> TYPE: DNA
<213> ORGANISM: Artificial Sequence
<220> FEATURE:
<223> OTHER INFORMATION: Description of Artificial Sequence:  Synthetic
      Sequence

<400> SEQUENCE: 4
atatatatgg gaggacgatg cgg                                          23

<210> SEQ ID NO 5
<211> LENGTH: 24
<212> TYPE: DNA
<213> ORGANISM: Artificial Sequence
<220> FEATURE:
<223> OTHER INFORMATION: Description of Artificial Sequence:  Synthetic
      Sequence

<400> SEQUENCE: 5
tttttttttc ccgctcgtcg tctg                                         24

<210> SEQ ID NO 6
<211> LENGTH: 76
<212> TYPE: DNA
<213> ORGANISM: Artificial Sequence
<220> FEATURE:
<223> OTHER INFORMATION: Description of Artificial Sequence:  Synthetic
      Sequence
<221> NAME/KEY: misc_feature
<222> LOCATION: (19)..(58)
<223> OTHER INFORMATION: N at positions 19-58 is A, C, G or T

<400> SEQUENCE: 6
ggctgatgac gtagcggcnn nnnnnnnnn nnnnnnnnnn nnnnnnnnnn nnnnnnnncc   60
gaaaggaaca acagag                                                  76

<210> SEQ ID NO 7
<211> LENGTH: 92
<212> TYPE: DNA
```

<213> ORGANISM: Artificial Sequence
<220> FEATURE:
<223> OTHER INFORMATION: Description of Artificial Sequence: Synthetic
      Sequence
<221> NAME/KEY: misc_feature
<222> LOCATION: (27)..(66)
<223> OTHER INFORMATION: N at positions 27-66 is A, C, G or T

<400> SEQUENCE: 7
atatatatgg ctgatgacgt agcggcnnnn nnnnnnnnnn nnnnnnnnnn nnnnnnnnnn    60
nnnnnnccga aggaacaac agagaaaaaa aa                                   92

<210> SEQ ID NO 8
<211> LENGTH: 92
<212> TYPE: DNA
<213> ORGANISM: Artificial Sequence
<220> FEATURE:
<223> OTHER INFORMATION: Description of Artificial Sequence: Synthetic
      Sequence
<221> NAME/KEY: misc_feature
<222> LOCATION: (27)..(66)
<223> OTHER INFORMATION: N at positions 27-66 is A, C, G or T

<400> SEQUENCE: 8
atatatatgc cgtagtgatc gctcggnnnn nnnnnnnnnn nnnnnnnnnn nnnnnnnnnn    60
nnnnnngcga aacgacaaga agacaaaaaa aa                                  92

<210> SEQ ID NO 9
<211> LENGTH: 92
<212> TYPE: DNA
<213> ORGANISM: Artificial Sequence
<220> FEATURE:
<223> OTHER INFORMATION: Description of Artificial Sequence: Synthetic
      Sequence
<221> NAME/KEY: misc_feature
<222> LOCATION: (27)..(66)
<223> OTHER INFORMATION: N at positions 27-66 is A, C, G or T

<400> SEQUENCE: 9
atatatatcg tgtgagctgc tggccgnnnn nnnnnnnnnn nnnnnnnnnn nnnnnnnnnn    60
nnnnnnccga caggaagagc acacaaaaaa aa                                  92

<210> SEQ ID NO 10
<211> LENGTH: 92
<212> TYPE: DNA
<213> ORGANISM: Artificial Sequence
<220> FEATURE:
<223> OTHER INFORMATION: Description of Artificial Sequence: Synthetic
      Sequence
<221> NAME/KEY: misc_feature
<222> LOCATION: (27)..(66)
<223> OTHER INFORMATION: N at positions 27-66 is A, C, G or T

<400> SEQUENCE: 10
atatatatgc ggatcagctt gcaccgnnnn nnnnnnnnnn nnnnnnnnnn nnnnnnnnnn    60
nnnnnngcca gaagcagaag gacgaaaaaa aa                                  92

<210> SEQ ID NO 11
<211> LENGTH: 92
<212> TYPE: DNA
<213> ORGANISM: Artificial Sequence
<220> FEATURE:
<223> OTHER INFORMATION: Description of Artificial Sequence: Synthetic
      Sequence
<221> NAME/KEY: misc_feature
<222> LOCATION: (27)..(66)
<223> OTHER INFORMATION: N at positions 27-66 is A, C, G or T

<400> SEQUENCE: 11
atatatatcg tcgcagctgg cgctggnnnn nnnnnnnnnn nnnnnnnnnn nnnnnnnnnn    60
nnnnnnggga acacagacga ccgcaaaaaa aa    92

<210> SEQ ID NO 12
<211> LENGTH: 92
<212> TYPE: DNA
<213> ORGANISM: Artificial Sequence
<220> FEATURE:
<223> OTHER INFORMATION: Description of Artificial Sequence: Synthetic
      Sequence
<221> NAME/KEY: misc_feature
<222> LOCATION: (27)..(66)
<223> OTHER INFORMATION: N at positions 27-66 is A, C, G or T

<400> SEQUENCE: 12
atatatatcg cgcagctgcc tgtcgcnnnn nnnnnnnnnn nnnnnnnnnn nnnnnnnnnn    60
nnnnnnggca gacagcaaca cgggaaaaaa aa    92

<210> SEQ ID NO 13
<211> LENGTH: 92
<212> TYPE: DNA
<213> ORGANISM: Artificial Sequence
<220> FEATURE:
<223> OTHER INFORMATION: Description of Artificial Sequence: Synthetic
      Sequence
<221> NAME/KEY: misc_feature
<222> LOCATION: (27)..(66)
<223> OTHER INFORMATION: N at positions 27-66 is A, C, G or T

<400> SEQUENCE: 13
atatatatgc gtgccgtcgc ggcccgnnnn nnnnnnnnnn nnnnnnnnnn nnnnnnnnnn    60
nnnnnncgga gcagcaggca caccaaaaaa aa    92

<210> SEQ ID NO 14
<211> LENGTH: 110
<212> TYPE: DNA
<213> ORGANISM: Artificial Sequence
<220> FEATURE:
<223> OTHER INFORMATION: Description of Artificial Sequence: Synthetic
      Sequence
<221> NAME/KEY: misc_feature
<222> LOCATION: (27)..(66)
<223> OTHER INFORMATION: N at positions 27-66 is A, C, G or T

<400> SEQUENCE: 14
atatatatgc gggcgtccgt gcggtcnnnn nnnnnnnnnn nnnnnnnnnn nnnnnnnnnn    60
nnnnnngagc cacgccacag caggaaaaaa aaggctgatg acgtagcggc    110

<210> SEQ ID NO 15
<211> LENGTH: 18
<212> TYPE: DNA
<213> ORGANISM: Artificial Sequence
<220> FEATURE:
<223> OTHER INFORMATION: Description of Artificial Sequence: Synthetic
      Sequence

<400> SEQUENCE: 15
ggctgatgac gtagcggc    18

<210> SEQ ID NO 16
<211> LENGTH: 26
<212> TYPE: DNA
<213> ORGANISM: Artificial Sequence

```
<220> FEATURE:
<223> OTHER INFORMATION: Description of Artificial Sequence: Synthetic
      Sequence

<400> SEQUENCE: 16
atatatatgg ctgatgacgt agcggc                                              26

<210> SEQ ID NO 17
<211> LENGTH: 26
<212> TYPE: DNA
<213> ORGANISM: Artificial Sequence
<220> FEATURE:
<223> OTHER INFORMATION: Description of Artificial Sequence: Synthetic
      Sequence

<400> SEQUENCE: 17
atatatatgc cgtagtgatc gctcgg                                              26

<210> SEQ ID NO 18
<211> LENGTH: 26
<212> TYPE: DNA
<213> ORGANISM: Artificial Sequence
<220> FEATURE:
<223> OTHER INFORMATION: Description of Artificial Sequence: Synthetic
      Sequence

<400> SEQUENCE: 18
atatatatcg tgtgagctgc tggccg                                              26

<210> SEQ ID NO 19
<211> LENGTH: 26
<212> TYPE: DNA
<213> ORGANISM: Artificial Sequence
<220> FEATURE:
<223> OTHER INFORMATION: Description of Artificial Sequence: Synthetic
      Sequence

<400> SEQUENCE: 19
atatatatgc ggatcagctt gcaccg                                              26

<210> SEQ ID NO 20
<211> LENGTH: 26
<212> TYPE: DNA
<213> ORGANISM: Artificial Sequence
<220> FEATURE:
<223> OTHER INFORMATION: Description of Artificial Sequence: Synthetic
      Sequence

<400> SEQUENCE: 20
atatatatcg tcgcagctgg cgctgg                                              26

<210> SEQ ID NO 21
<211> LENGTH: 26
<212> TYPE: DNA
<213> ORGANISM: Artificial Sequence
<220> FEATURE:
<223> OTHER INFORMATION: Description of Artificial Sequence: Synthetic
      Sequence

<400> SEQUENCE: 21
atatatatcg cgcagctgcc tgtcgc                                              26

<210> SEQ ID NO 22
<211> LENGTH: 26
<212> TYPE: DNA
<213> ORGANISM: Artificial Sequence
<220> FEATURE:
```

<223> OTHER INFORMATION: Description of Artificial Sequence: Synthetic
      Sequence

<400> SEQUENCE: 22
atatatatgc gtgccgtcgc ggcccg                                    26

<210> SEQ ID NO 23
<211> LENGTH: 26
<212> TYPE: DNA
<213> ORGANISM: Artificial Sequence
<220> FEATURE:
<223> OTHER INFORMATION: Description of Artificial Sequence: Synthetic
      Sequence

<400> SEQUENCE: 23
atatatatgc gggcgtccgt gcggtc                                    26

<210> SEQ ID NO 24
<211> LENGTH: 18
<212> TYPE: DNA
<213> ORGANISM: Artificial Sequence
<220> FEATURE:
<223> OTHER INFORMATION: Description of Artificial Sequence: Synthetic
      Sequence

<400> SEQUENCE: 24
ctctgttgtt cctttcgg                                             18

<210> SEQ ID NO 25
<211> LENGTH: 26
<212> TYPE: DNA
<213> ORGANISM: Artificial Sequence
<220> FEATURE:
<223> OTHER INFORMATION: Description of Artificial Sequence: Synthetic
      Sequence

<400> SEQUENCE: 25
ttttttttct ctgttgttcc tttcgg                                    26

<210> SEQ ID NO 26
<211> LENGTH: 26
<212> TYPE: DNA
<213> ORGANISM: Artificial Sequence
<220> FEATURE:
<223> OTHER INFORMATION: Description of Artificial Sequence: Synthetic
      Sequence

<400> SEQUENCE: 26
ttttttttgt cttcttgtcg tttcgc                                    26

<210> SEQ ID NO 27
<211> LENGTH: 26
<212> TYPE: DNA
<213> ORGANISM: Artificial Sequence
<220> FEATURE:
<223> OTHER INFORMATION: Description of Artificial Sequence: Synthetic
      Sequence

<400> SEQUENCE: 27
ttttttttgt gtgctcttcc tgtcgg                                    26

<210> SEQ ID NO 28
<211> LENGTH: 26
<212> TYPE: DNA
<213> ORGANISM: Artificial Sequence
<220> FEATURE:
<223> OTHER INFORMATION: Description of Artificial Sequence: Synthetic -continued

```
    Sequence

<400> SEQUENCE: 28 tttttttttcg tccttctgct tctggc                                              26

<210> SEQ ID NO 29
<211> LENGTH: 26
<212> TYPE: DNA
<213> ORGANISM: Artificial Sequence
<220> FEATURE:
<223> OTHER INFORMATION: Description of Artificial Sequence:  Synthetic
      Sequence

<400> SEQUENCE: 29 tttttttttgc ggtcgtctgt gttccc                                              26

<210> SEQ ID NO 30
<211> LENGTH: 26
<212> TYPE: DNA
<213> ORGANISM: Artificial Sequence
<220> FEATURE:
<223> OTHER INFORMATION: Description of Artificial Sequence:  Synthetic
      Sequence

<400> SEQUENCE: 30 tttttttttcc cgtgttgctg tctgcc                                              26

<210> SEQ ID NO 31
<211> LENGTH: 26
<212> TYPE: DNA
<213> ORGANISM: Artificial Sequence
<220> FEATURE:
<223> OTHER INFORMATION: Description of Artificial Sequence:  Synthetic
      Sequence

<400> SEQUENCE: 31 tttttttttgg tgtgcctgct gctccg                                              26

<210> SEQ ID NO 32
<211> LENGTH: 26
<212> TYPE: DNA
<213> ORGANISM: Artificial Sequence
<220> FEATURE:
<223> OTHER INFORMATION: Description of Artificial Sequence:  Synthetic
      Sequence

<400> SEQUENCE: 32 tttttttttcc tgctgtggcg tggctc                                              26
                                                                            1
```

METHOD FOR THE AUTOMATED GENERATION OF NUCLEIC ACID LIGANDS

RELATED APPLICATIONS

This application is a continuation-in-part application of U.S. patent application Ser. No. 09/616,284, filed Jul. 14, 2000, which is a continuation-in-part application of U.S. patent application Ser. No. 09/356,233, filed Jul. 16, 1999, which is a continuation-in-part application of U.S. patent application Ser. No. 09/232,946, filed Jan. 19, 1999, now U.S. Pat. No. 6,569,620, each of which is entitled "Method and Apparatus for the Automated Generation of Nucleic Acid Ligands".

FIELD OF THE INVENTION

This invention is directed to a method for the generation of nucleic acid ligands having specific functions against target molecules using the SELEX process. The methods described herein enable nucleic acid ligands to be generated in dramatically shorter times and with much less operator intervention than was previously possible using prior art techniques. The invention includes a device capable of generating nucleic acid ligands with little or no operator intervention. The invention also includes reagents that can be used in any automated nucleic acid selection procedure to prevent the formation of high molecular weight amplification artifacts.

BACKGROUND OF THE INVENTION

The dogma for many years was that nucleic acids had primarily an informational role. Through a method known as Systematic Evolution of Ligands by EXponential enrichment, termed the SELEX process, it has become clear that nucleic acids have three dimensional structural diversity not unlike proteins. The SELEX process is a method for the in vitro evolution of nucleic acid molecules with highly specific binding to target molecules and is described in U.S. patent application Ser. No. 07/536,428, filed Jun. 11, 1990, entitled "Systematic Evolution of Ligands by EXponential Enrichment," now abandoned, U.S. Pat. No. 5,475,096 entitled "Nucleic Acid Ligands", and U.S. Pat. No. 5,270,163 (see also WO 91/19813) entitled "Nucleic Acid Ligands" each of which is specifically incorporated by reference herein. Each of these patents and applications, collectively referred to herein as the SELEX Patent Applications, describes a fundamentally novel method for making a nucleic acid ligand to any desired target molecule. The SELEX process provides a class of products which are referred to as nucleic acid ligands or aptamers, each having a unique sequence, and which has the property of binding specifically to a desired target compound or molecule. Each SELEX-identified nucleic acid ligand is a specific ligand of a given target compound or molecule.

The SELEX process is based on the unique insight that nucleic acids have sufficient capacity for forming a variety of two- and three-dimensional structures and sufficient chemical versatility available within their monomers to act as ligands (form specific binding pairs) with virtually any chemical compound, whether monomeric or polymeric. Molecules of any size or composition can serve as targets. The SELEX method applied to the application of high affinity binding involves selection from a mixture of candidate oligonucleotides and step-wise iterations of binding, partitioning and amplification, using the same general selection scheme, to achieve virtually any desired criterion of binding affinity and selectivity. Starting from a mixture of nucleic acids, preferably comprising a segment of randomized sequence, the SELEX method includes steps of contacting the mixture with the target under conditions favorable for binding, partitioning unbound nucleic acids from those nucleic acids which have bound specifically to target molecules, dissociating the nucleic acid-target complexes, amplifying the nucleic acids dissociated from the nucleic acid-target complexes to yield a ligand-enriched mixture of nucleic acids, then reiterating the steps of binding, partitioning, dissociating and amplifying through as many cycles as desired to yield highly specific high affinity nucleic acid ligands to the target molecule.

It has been recognized by the present inventors that the SELEX method demonstrates that nucleic acids as chemical compounds can form a wide array of shapes, sizes and configurations, and are capable of a far broader repertoire of binding and other functions than those displayed by nucleic acids in biological systems. The present inventors have recognized that SELEX or SELEX-like processes could be used to identify nucleic acids which can facilitate any chosen reaction in a manner similar to that in which nucleic acid ligands can be identified for any given target. In theory, within a candidate mixture of approximately $10^{13}$ to $10^{18}$ nucleic acids, the present inventors postulate that at least one nucleic acid exists with the appropriate shape to facilitate each of a broad variety of physical and chemical interactions.

The basic SELEX method has been modified to achieve a number of specific objectives. For example, U.S. patent application Ser. No. 07/960,093, filed Oct. 14, 1992, now abandoned, and U.S. Pat. No. 5,707,796, both entitled "Method for Selecting Nucleic Acids on the Basis of Structure," describe the use of the SELEX process in conjunction with gel electrophoresis to select nucleic acid molecules with specific structural characteristics, such as bent DNA. U.S. patent application Ser. No. 08/123,935, filed Sep. 17, 1993, and U.S. patent application Ser. No. 08/443,959 filed May 18, 1995, both entitled "Photoselection of Nucleic Acid Ligands," and both now abandoned, and U.S. Pat. Nos. 5,763,177, U.S. patent application Ser. No. 6,001,577, WO 95/08003, U.S. Pat. No. 6,291,184, U.S. Pat. No. 6,458,539, and U.S. patent application Ser. No. 09/723,718, filed Nov. 28, 2000, each of which is entitled "Systematic Evolution of Nucleic Acid Ligands by Exponential Enrichment: Photoselection of Nucleic Acid Ligands and Solution SELEX," all describe a SELEX process-based method for selecting nucleic acid ligands containing photoreactive groups capable of binding and/or photocrosslinking to and/or photoinactivating a target molecule. The resulting nucleic acid ligands are often referred to as "photoaptamers." These patents and patent applications are referred to in this application collectively as "the photoSELEX process applications." In the photoSELEX process variation of the SELEX process, a modified nucleotide activated by absorption of light is incorporated in place of a native base in either RNA- or in ssDNA-randomized oligonucleotide libraries.

U.S. Pat. No. 5,580,737 entitled "High-Affinity Nucleic Acid Ligands That Discriminate Between Theophylline and Caffeine," describes a method for identifying highly specific nucleic acid ligands able to discriminate between closely related molecules, termed Counter-SELEX. U.S. Pat. No. 5,567,588 entitled "Systematic Evolution of Ligands by EXponential Enrichment: Solution SELEX," describes a SELEX-based method which achieves highly efficient partitioning between oligonucleotides having high and low affinity for a target molecule. U.S. Pat. No. 5,496,938 entitled "Nucleic Acid Ligands to HIV-RT and HIV-1 Rev,"

describes methods for obtaining improved nucleic acid ligands after SELEX has been performed. U.S. Pat. No. 5,705,337 entitled "Systematic Evolution of Ligands by Exponential Enrichment: Chemi-SELEX," describes methods for covalently linking a ligand to its target.

The SELEX method encompasses the identification of high-affinity nucleic acid ligands containing modified nucleotides conferring improved characteristics on the ligand, such as improved in vivo stability or improved delivery characteristics. Examples of such modifications include chemical substitutions at the ribose and/or phosphate and/or base positions. SELEX process-identified nucleic acid ligands containing modified nucleotides are described in U.S. Pat. No. 5,660,985 entitled "High Affinity Nucleic Acid Ligands Containing Modified Nucleotides," that describes oligonucleotides containing nucleotide derivatives chemically modified at the 5- and 2'-positions of pyrimidines. U.S. Pat. No. 5,580,737, supra, describes highly specific nucleic acid ligands containing one or more nucleotides modified with 2'-amino (2'-NH$_2$), 2'-fluoro (2'-F), and/or 2'-O-methyl (2'-OMe). U.S. patent application Ser. No. 08/264,029, filed Jun. 22, 1994, entitled "Novel Method of Preparation of Known and Novel 2' Modified Nucleosides by Intramolecular Nucleophilic Displacement," describes oligonucleotides containing various 2'-modified pyrimidines.

The SELEX method encompasses combining selected oligonucleotides with other selected oligonucleotides and non-oligonucleotide functional units as described in U.S. Pat. No. 5,637,459 entitled "Systematic Evolution of Ligands by EXponential Enrichment: Chimeric SELEX," and U.S. Pat. No. 5,683,867 entitled "Systematic Evolution of Ligands by EXponential Enrichment: Blended SELEX," respectively. These applications allow the combination of the broad array of shapes and other properties, and the efficient amplification and replication properties, of oligonucleotides with the desirable properties of other molecules.

The SELEX method further encompasses combining selected nucleic acid ligands with lipophilic compounds or non-immunogenic, high molecular weight compounds in a diagnostic or therapeutic complex as described in U.S. Pat. No. 6,011,020 entitled "Nucleic Acid Ligand Complexes".

Nucleic acid ligands may be attached to the surface of solid supports to form microarrays. Such microarrays (also commonly referred to as "biochips"), and methods for their manufacture and use, are described in U.S. Pat. No. 6,242,246 U.S. patent application Ser. No. 08/211,680, filed December 14, 1998, now abandoned, WO 99/31275, U.S. Pat. No. 6,544,776, U.S. Pat. No. 6,503,715, and U.S. Pat. No. 6,458,543, each of which is entitled "Nucleic Acid Ligand Diagnostic Biochip." These patents are collectively as referred to herein as "the biochip applications."

One potential problem encountered in the diagnostic use of nucleic acids is that oligonucleotides in their phosphodiester form may be quickly degraded in body fluids by intracellular and extracellular enzymes such as endonucleases and exonucleases before the desired effect is manifest. Certain chemical modifications of the nucleic acid ligand can be made to increase the in vivo stability of the nucleic acid ligand or to enhance or to mediate the delivery of the nucleic acid ligand. See, e.g., U.S. patent application Ser. No. 08/117,991, filed Sep. 9, 1993, now abandoned, and U.S. Pat. No. 5,660,985, both entitled "High Affinity Nucleic Acid Ligands Containing Modified Nucleotides", and U.S. Pat. No. 6,387,620, entitled "Transcription-free SELEX", each of which is specifically incorporated herein by reference. Modifications of the nucleic acid ligands contemplated in this invention include, but are not limited to, those which provide other chemical groups that incorporate additional charge, polarizability, hydrophobicity, hydrogen bonding, electrostatic interaction, and fluxionality to the nucleic acid ligand bases or to the nucleic acid ligand as a whole. Such modifications include, but are not limited to, 2'-position sugar modifications, 5-position pyrimidine modifications, 8-position purine modifications, modifications at exocyclic amines, substitution of 4-thiouridine, substitution of 5-bromo or 5-iodo-uracil; backbone modifications, phosphorothioate or alkyl phosphate modifications, methylations, unusual base-pairing combinations such as the isobases isocytidine and isoguanidine and the like. Modifications can also include 3' and 5' modifications such as capping. In preferred embodiments of the instant invention, the nucleic acid ligands are DNA molecules that are modified with a photoreactive group on 5-position of pyrimidine residues. The modifications can be pre- or post-SELEX process modifications.

Each of the above described patent applications, many of which describe modifications of the basic SELEX procedure, are specifically incorporated by reference herein in their entirety.

Given the unique ability of the SELEX process to provide ligands for virtually any target molecule, it would be highly desirable to have an automated, high-throughput method for generating nucleic acid ligands.

SUMMARY OF THE INVENTION

The present invention includes methods and apparatus for the automated generation of nucleic acid ligands against virtually any target molecule. This process is termed the automated SELEX process. In its most basic embodiment, the method uses a robotic manipulator to move reagents to one or more work stations on a work surface where the individual steps of the SELEX process are performed. The individual steps include: 1) contacting the candidate nucleic acid ligands with the target molecule(s) of interest immobilized on a solid support; 2) partitioning the nucleic acid ligands that have interacted in the desired way with the target molecule on the solid support away from those nucleic acids that have failed to do so; and 3) amplifying the nucleic acid ligands that have interacted with the target molecule. Steps 1–3 are performed for the desired number of cycles by the automated SELEX process and apparatus; the resulting nucleic acid ligands are then isolated and purified.

Step 3 is performed with novel primers and candidate mixtures that minimize the formation of high molecular weight artifacts termed "parasites." While not wishing to be bound by any one theory, it is believed that such parasites arise from rare mispriming events during the amplification process, and are propagated to subsequent rounds of the automated SELEX process—where they continue to grow in size and number—unless they are size-fractionated from nucleic acid ligands at the conclusion of step 3. Size-fractionation procedures, such as gel electrophoresis, are time-consuming and difficult to automate. The primers and candidate mixtures provided herein drastically reduce the frequency of the intial mispriming event, and also drastically reduce the subsequent propagation of any rare parasites that do form. As a result, the automated SELEX process can be performed without size-fractionation procedures. The elimination of size-fractionation procedures greatly contributes to the utility, efficiency, and ease of operation of the automated SELEX process. Moreover, the techniques and procedures described herein and the primers and candidate mixtures provided by the instant invention will also be useful in any nucleic acid selection process that employs nucleic acid amplification without size-fractionation.

The automated SELEX process described herein enables the generation of large pools of nucleic acid ligands with little or no operator intervention. In particular, the methods provided by this invention will allow high affinity nucleic acid ligands to be generated routinely in just a few days, rather than over a period of weeks or even months as was previously required. The highly parallel nature of the automated SELEX process allows the simultaneous isolation of ligands against diverse targets in a single automated SELEX process experiment. Similarly, the automated SELEX process can be used to generate nucleic acid ligands against a single target using many different selection conditions in a single experiment. The present invention greatly enhances the power of the SELEX process, and will make SELEX the routine method for the isolation of ligands.

DETAILED DESCRIPTION OF THE FIGURES

FIG. 1 demonstrates the effect of blocking reagents on background binding of RNA to microtiter plates. The total number of RNA molecules remaining in wells of an Immulon 1 polystyrene plate, quantified with qPCR as described below are displayed for wells treated with various blocking reagents, (1) SHMCK alone, (2) SuperBlock, (3) SCHMK+ Iblock, (4) SCHMK+SuperBlock, (5) SCHMK+Casein, (6) SCHMK+BSA.

FIG. 2 demonstrates the effect of buffer reagents on background binding of RNA to microtiter plates. The total number of RNA molecules remaining in unblocked wells of an Immulon 1 polystyrene plate, quantified with qPCR as described below are displayed for wells incubated and washed with solutions containing various buffer reagents, (1) SHMCK+0.1% Iblock+0.05% Tween 20 (SIT), (2) SHMCK+0.01% HSA (SA), (3) SCHMK+0.05% Tween 20 (ST), (4) SCHMK+0.01% HSA+0.05% Tween 20 (SAT), (5) SCHMK.

FIG. 3 depicts the quantification of passive adsorption of murine PS-Rg to Immulon 1 polystyrene plates. The amount of PS-Rg capable of binding aptamer 1901 after protein immobilization through hydrophobic interactions (filled circles) is displayed as a function of input protein concentration. The amount of active protein was obtained from the plateau values of aptamer binding curves.

FIG. 4 depicts the binding and EDTA elution of aptamer 1901 from murine PS-Rg passively hydrophobically attached to an Immulon 1 polystyrene plate. Total binding of $^{32}$P-labeled aptamer 1901 to wells coated with murine PS-Rg, loaded at 4.0 µg/ml, is plotted as a function of total aptamer concentration (filled circles). The amount of eluted aptamer for each of these concentrations is shown by filled triangles, and the amount of aptamer remaining in the protein coated wells after elution is shown by open circles. All samples were quantified by scintillation counting of $^{32}$P.

FIG. 5 depicts the progress of the automated in vitro selection process. The number of RNA molecules eluted from plate wells for both manual (squares) and automated (circles) experiments are displayed for each of five rounds of SELEX performed. The amount of RNA eluted from protein coated wells is denoted by the filled markers and background binding RNA is denoted by open markers, and the amount of coated protein used in each round is denoted by x markers.

Figure 12:
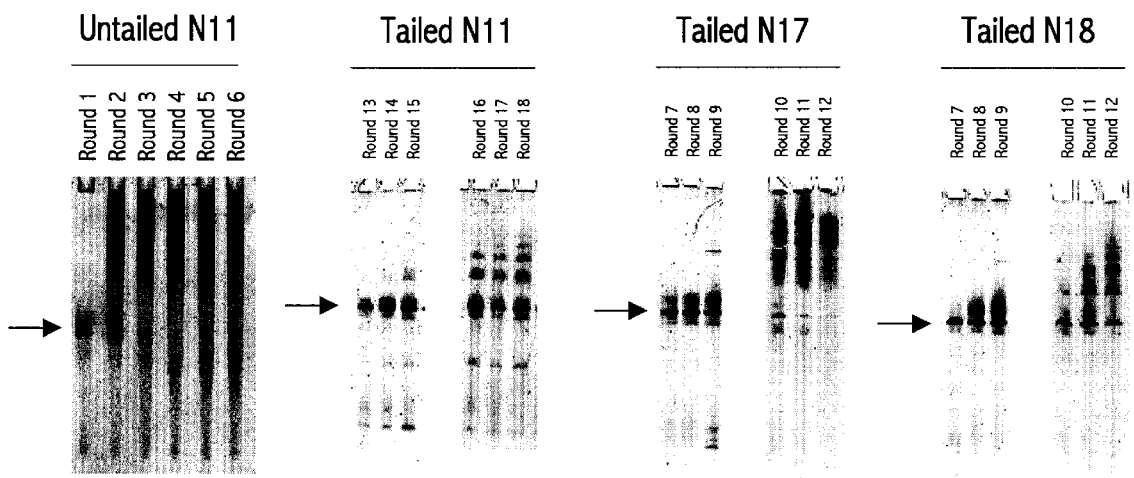

FIG. 12 shows examples of SELEX processes carried out with untailed and tailed PCR primers. High molecular weight parasites of the PCR process are generated within one round of the SELEX process when untailed primers are used. Parasites do not arise until Rounds 10–15 for the tailed primers.

Figure 13:
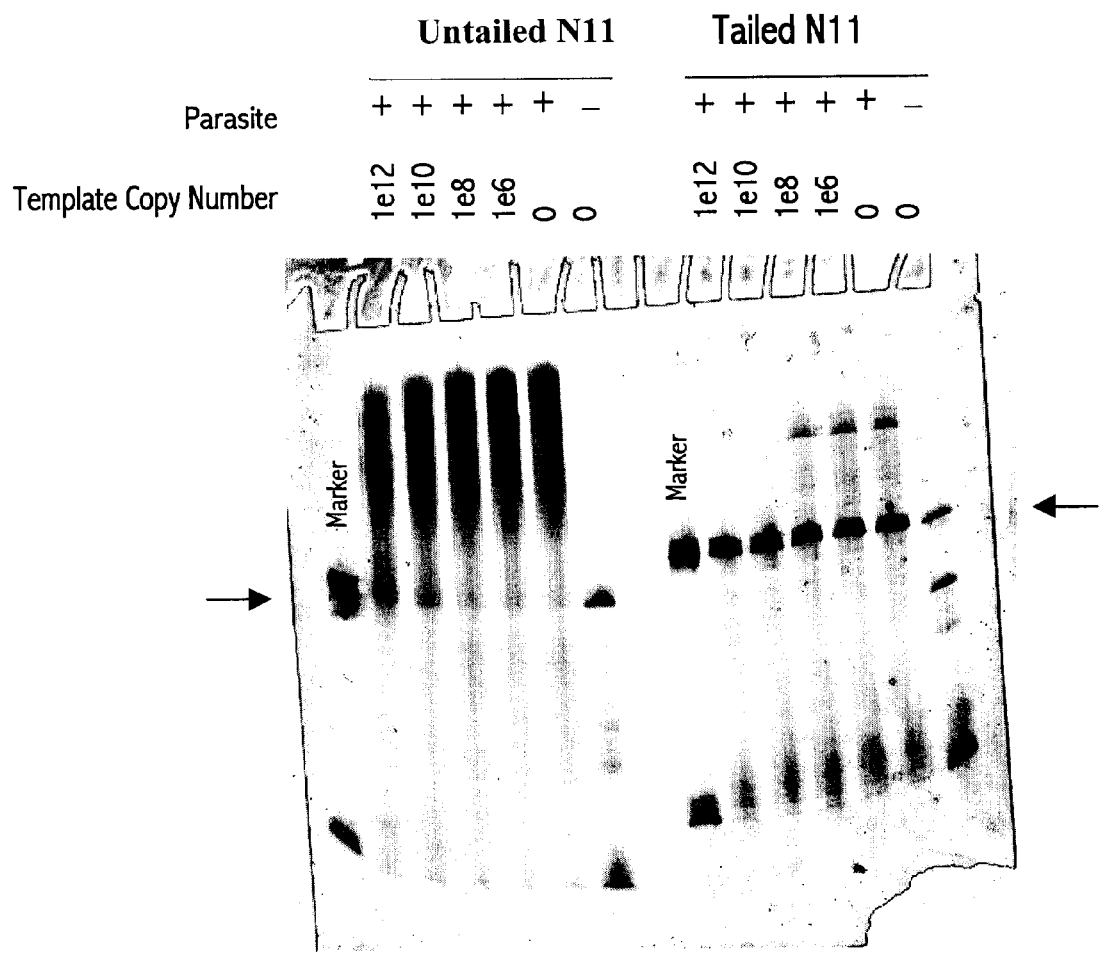

FIG. 13 shows that parasites that eventually arise in PCR reactions using tailed primers do not dominate those reactions, even when template is present at low copy numbers.

Figure 14:
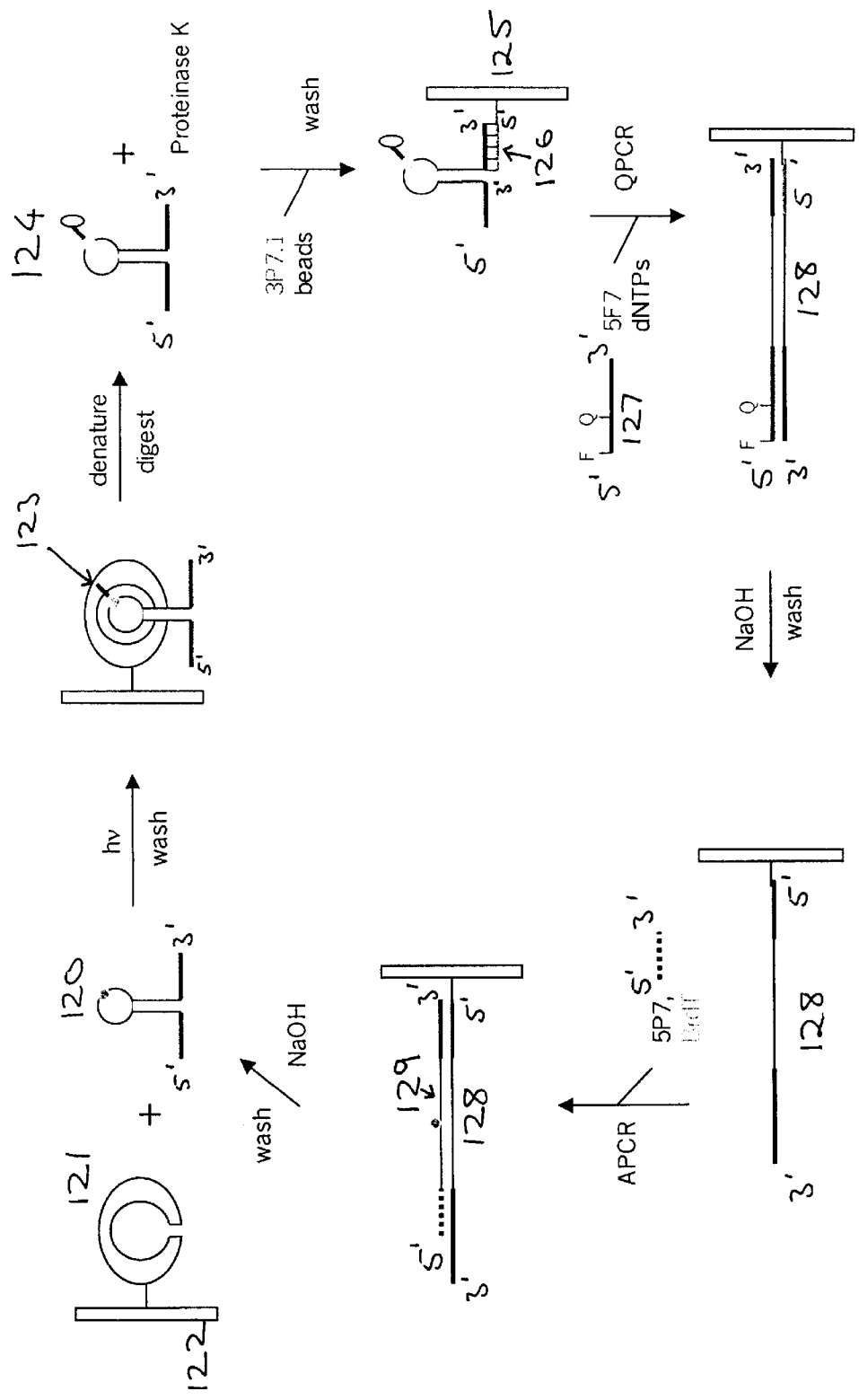

FIG. 14 shows an embodiment of the automated photoSELEX process.

Figure 15:
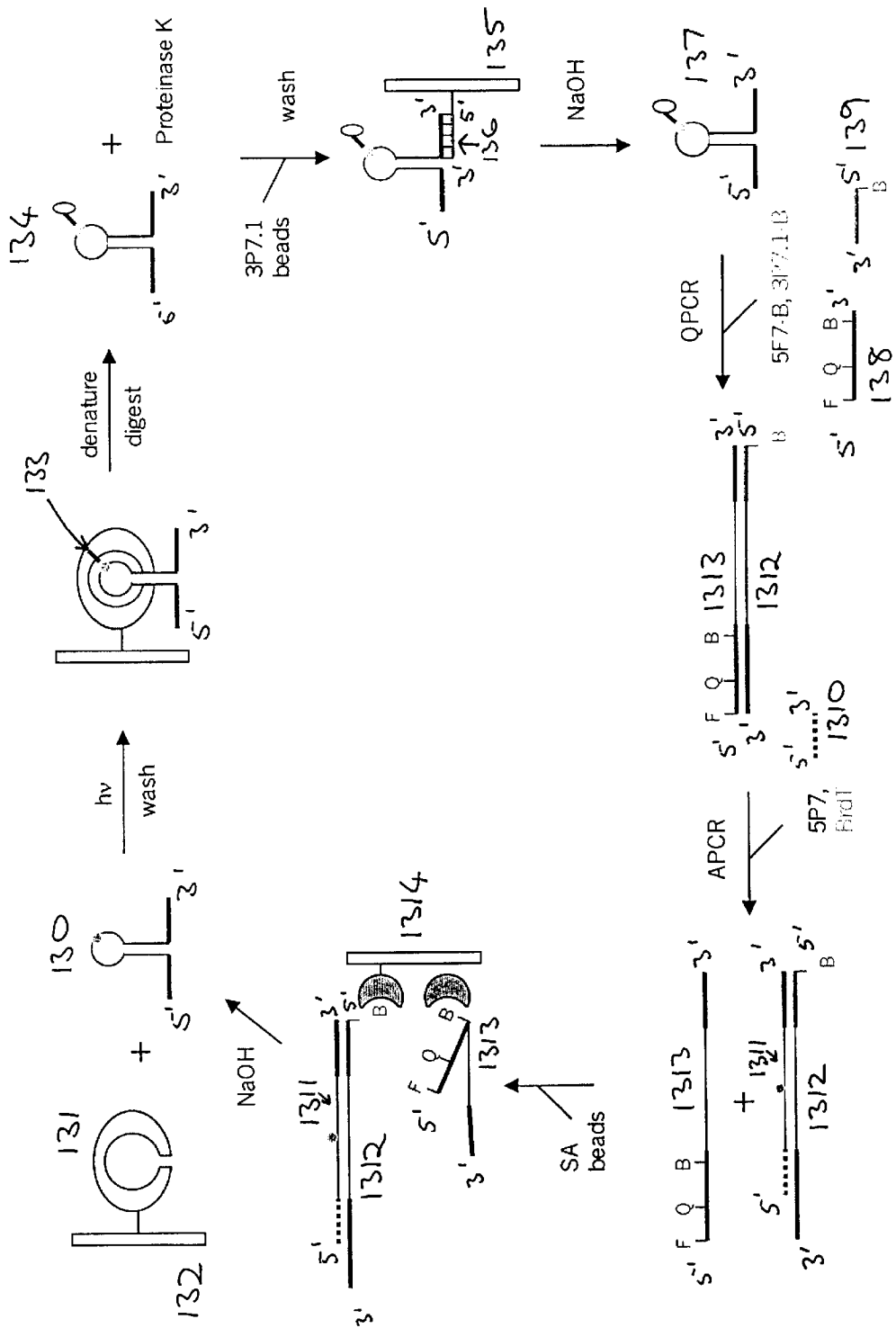

FIG. 15 shows another embodiment of the automated photoSELEX process.

Figure 16:
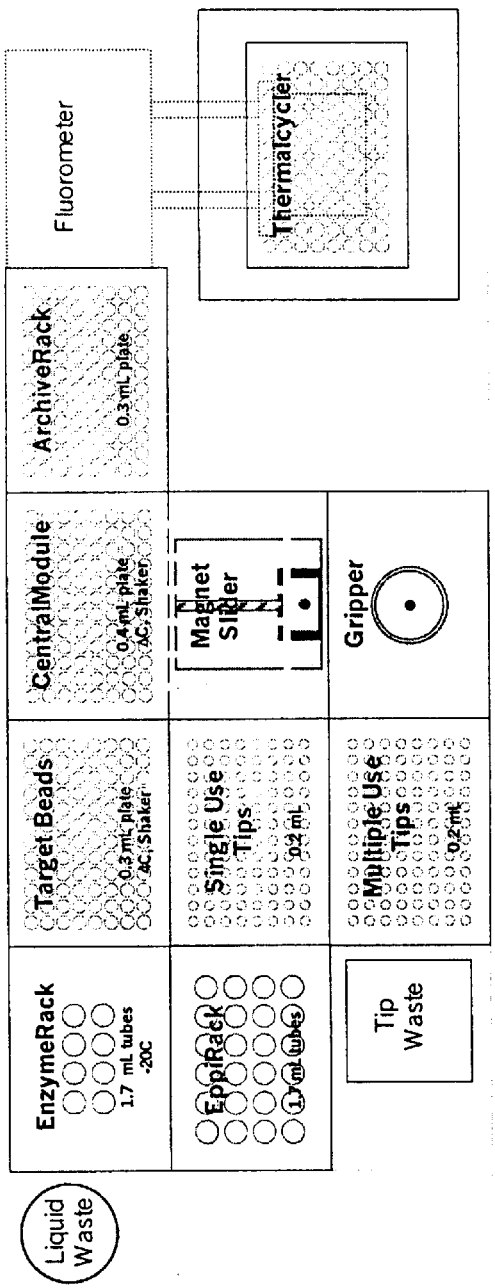

FIG. 16 shows one embodiment of an automated SELEX work surface in plan view.

DETAILED DESCRIPTION OF THE INVENTION

Definitions

Various terms are used herein to refer to aspects of the present invention. To aid in the clarification of the description of the components of this invention, the following definitions are provided:

As used herein, "nucleic acid ligand" is a non-naturally occurring nucleic acid having a desirable action on a target. Nucleic acid ligands are also sometimes referred to in this applications as "aptamers" or "clones." A desirable action includes, but is not limited to, binding of the target, catalytically changing the target, reacting with the target in a way which modifies/alters the target or the functional activity of the target, covalently attaching to the target as in a suicide inhibitor, facilitating the reaction between the target and another molecule. In the preferred embodiment, the action is specific binding affinity for a target molecule, such target molecule being a three dimensional chemical structure other than a polynucleotide that binds to the nucleic acid ligand through a mechanism which predominantly depends on Watson/Crick base pairing or triple helix binding, wherein the nucleic acid ligand is not a nucleic acid having the known physiological function of being bound by the target molecule. Nucleic acid ligands include nucleic acids that are identified from a candidate mixture of nucleic acids, said nucleic acid ligand being a ligand of a given target, by the method comprising: a) contacting the candidate mixture with the target, wherein nucleic acids having an increased affinity to the target relative to the candidate mixture may be partitioned from the remainder of the candidate mixture; b) partitioning the increased affinity nucleic acids from the remainder of the candidate mixture; and c) amplifying the increased affinity nucleic acids to yield a ligand-enriched mixture of nucleic acids, whereby nucleic acid ligands of the target molecule are identified.

As used herein, "candidate mixture" is a mixture of nucleic acids of differing sequence from which to select a desired ligand. The source of a candidate mixture can be from naturally-occurring nucleic acids or fragments thereof, chemically synthesized nucleic acids, enzymatically synthesized nucleic acids or nucleic acids made by a combination of the foregoing techniques. In this invention, candidate mixture is also sometimes referred to as "pool." For example, "RNA pool" refers to a candidate mixture comprised of RNA.

In a preferred embodiment, each nucleic acid has fixed sequences surrounding a randomized region to facilitate the amplification process. As detailed in the rest of this application, the candidate mixture nucleic acids can further comprise fixed "tail" sequences at their 5' and 3' termini to prevent the formation of high molecular weight parasites of the amplification process.

As used herein, "nucleic acid" means either DNA, RNA, single-stranded or double-stranded, and any chemical modifications thereof. Modifications include, but are not limited to, those which provide other chemical groups that incorporate additional charge, polarizability, hydrogen bonding, electrostatic interaction, and fluxionality to the nucleic acid ligand bases or to the nucleic acid ligand as a whole. Such modifications include, but are not limited to, 2'-position sugar modifications, 5-position pyrimidine modifications, 8-position purine modifications, modifications at exocyclic amines, substitution of 4-thiouridine, substitution of 5-bromo or 5-iodo-uracil; backbone modifications, methylations, unusual base-pairing combinations such as the isobases isocytidine and isoguanidine and the like. Modifications can also include 3' and 5' modifications such as capping.

"SELEX" methodology involves the combination of selection of nucleic acid ligands which interact with a target in a desirable manner, for example binding to a protein, with amplification of those selected nucleic acids. Optional iterative cycling of the selection/amplification steps allows selection of one or a small number of nucleic acids which interact most strongly with the target from a pool which contains a very large number of nucleic acids. Cycling of the selection/amplification procedure is continued until a selected goal is achieved. The SELEX methodology is described in the SELEX Patent Applications.

"SELEX target" or "target molecule" or "target" refers herein to any compound upon which a nucleic acid can act in a predetermined desirable manner. A SELEX target molecule can be a protein, peptide, nucleic acid, carbohydrate, lipid, polysaccharide, glycoprotein, hormone, receptor, antigen, antibody, virus, pathogen, toxic substance, substrate, metabolite, transition state analog, cofactor, inhibitor, drug, dye, nutrient, growth factor, cell, tissue, etc., without limitation. Virtually any chemical or biological effector would be a suitable SELEX target. Molecules of any size can serve as SELEX targets. A target can also be modified in certain ways to enhance the likelihood of an interaction between the target and the nucleic acid.

"Tissue target" or "tissue" refers herein to a certain subset of the SELEX targets described above. According to this definition, tissues are macromolecules in a heterogeneous environment. As used herein, tissue refers to a single cell type, a collection of cell types, an aggregate of cells, or an aggregate of macromolecules. This differs from simpler SELEX targets which are typically isolated soluble molecules, such as proteins. In the preferred embodiment, tissues are insoluble macromolecules which are orders of magnitude larger than simpler SELEX targets. Tissues are complex targets made up of numerous macromolecules, each macromolecule having numerous potential epitopes. The different macromolecules which comprise the numerous epitopes can be proteins, lipids, carbohydrates, etc., or combinations thereof. Tissues are generally a physical array of macromolecules that can be either fluid or rigid, both in terms of structure and composition. Extracellular matrix is an example of a more rigid tissue, both structurally and compositionally, while a membrane bilayer is more fluid in structure and composition. Tissues are generally not soluble and remain in solid phase, and thus partitioning can be accomplished relatively easily. Tissue includes, but is not limited to, an aggregate of cells usually of a particular kind together with their intercellular substance that form one of the structural materials commonly used to denote the general cellular fabric of a given organ, e.g., kidney tissue, brain tissue. The four general classes of tissues are epithelial tissue, connective tissue, nerve tissue and muscle tissue.

Examples of tissues which fall within this definition include, but are not limited to, heterogeneous aggregates of macromolecule such as fibrin clots which are acellular; homogeneous or heterogeneous aggregates of cells; higher ordered structures containing cells which have a specific function, such as organs, tumors, lymph nodes, arteries, etc.; and individual cells. Tissues or cells can be in their natural environment, isolated, or in tissue culture. The tissue can be intact or modified. The modification can include numerous changes such as transformation, transfection, activation, and substructure isolation, e.g., cell membranes, cell nuclei, cell organelles, etc.

Sources of the tissue, cell or subcellular structures can be obtained from prokaryotes as well as eukaryotes. This includes human, animal, plant, bacterial, fungal and viral structures.

As used herein, "solid support" is defined as any surface to which molecules may be attached through either covalent or non-covalent bonds. This includes, but is not limited to, membranes, plastics, paramagnetic beads, charged paper, nylon, Langrnuir-Bodgett films, functionalized glass, germanium, silicon, PTFE, polystyrene, gallium arsenide, gold and silver. Any other material known in the art that is capable of having functional groups such as amino, carboxyl, thiol or hydroxyl incorporated on its surface, is also contemplated. This includes surfaces with any topology, including, but not limited to, spherical surfaces, grooved surfaces, and cylindrical surfaces (e.g., columns).

"Partitioning" means any process whereby ligands bound to target molecules can be separated from nucleic acids not bound to target molecules. More broadly stated, partitioning allows for the separation of all the nucleic acids in a candidate mixture into at least two pools based on their relative affinity to the target molecule. Partitioning can be accomplished by various methods known in the art. Nucleic acid-protein pairs can be bound to nitrocellulose filters while unbound nucleic acids are not. Columns which specifically retain nucleic acid-target complexes can be used for partitioning. For example, oligonucleotides able to associate with a target molecule bound on a column allow use of column chromatography for separating and isolating the highest affinity nucleic acid ligands. Beads upon which target molecules are conjugated can also be used to partition nucleic acid ligands in a mixture. If the beads are paramagnetic, then the partitioning can be achieved through application of a magnetic field. Surface plasmon resonance technology can be used to partition nucleic acids in a mixture by immobilizing a target on a sensor chip and flowing the mixture over the chip, wherein those nucleic acids having affinity for the target can be bound to the target, and the remaining nucleic acids can be washed away. Liquid-liquid partitioning can be used as well as filtration gel retardation, and density gradient centrifugation.

In its most basic form, the SELEX process may be defined by the following series of steps:

1) A candidate mixture of nucleic acids of differing sequence is prepared. The candidate mixture generally includes regions of fixed sequences (i.e., each of the members of the candidate mixture contains the same sequences in the same location) and regions of randomized sequences. The fixed sequence regions are selected either: a) to assist in the amplification steps described below; b) to mimic a sequence known to bind to the target; or c) to enhance the concentration of a given structural arrangement of the nucleic acids in the candidate mixture. The randomized sequences can be totally randomized (i.e., the probability of finding a base at any position being one in four) or only partially randomized (e.g., the probability of finding a base at any location can be selected at any level between 0 and 100 percent). In this application, additional fixed "tail" sequences are described that may be added to the 5' and 3' termini of the candidate mixture nucleic acids. The function of the "tail" sequences is to prevent the formation of high molecular weight artifacts of the amplification process from disrupting the SELEX process when the amplification process is not followed by size fractionation of the amplified mixture.

2) The candidate mixture is contacted with the selected target under conditions favorable for binding between the target and members of the candidate mixture. Under these circumstances, the interaction between the target and the nucleic acids of the candidate mixture can be considered as forming nucleic acid-target pairs between the target and those nucleic acids having the strongest affinity for the target.

3) The nucleic acids with the highest affinity for the target are partitioned from those nucleic acids with lesser affinity to the target. Because only an extremely small number of sequences (and possibly only one molecule of nucleic acid) corresponding to the highest affinity nucleic acids exist in the candidate mixture, it is generally desirable to set the partitioning criteria so that a certain amount of the nucleic acids in the candidate mixture are retained during partitioning.

4) Those nucleic acids selected during partitioning as having relatively higher affinity to the target are then amplified to create a new candidate mixture that is enriched in nucleic acids having a relatively higher affinity for the target.

5) By repeating the partitioning and amplifying steps above, the newly formed candidate mixture contains fewer and fewer unique sequences, and the average degree of affinity of the nucleic acids to the target will generally increase. Taken to its extreme, the SELEX process will yield a candidate mixture containing one or a small number of unique nucleic acids representing those nucleic acids from the original candidate mixture having the highest affinity to the target molecule.

As used herein, "PhotoSELEX" is an acronym for Photochemical Systematic Evolution of Ligands by EXponential enrichment, and refers to a variation of the SELEX process in which a modified nucleotide activated by absorption of light is incorporated in place of a native base in either RNA- or in ssDNA-randomized oligonucleotide libraries, the nucleic acid target molecule mixture is irradiated causing some nucleic acids incorporated in nucleic acid-target molecule complexes to crosslink to the target molecule via the photoreactive finctional groups, and the selection step is a selection for photocrosslinking activity.

The SELEX Patent Applications describe and elaborate on this process in great detail. Included are targets that can be used in the process; methods for the preparation of the initial candidate mixture; methods for partitioning nucleic acids within a candidate mixture; and methods for amplifying partitioned nucleic acids to generate enriched candidate mixtures. The SELEX Patent Applications also describe ligand solutions obtained to a number of target species, including protein targets wherein the protein is or is not a nucleic acid binding protein.

In one embodiment, the automated SELEX method or process uses one or more computer-controlled robotic manipulators to move solutions to and from a work station located on a work surface. The individual steps of the SELEX process are carried out at the work station. In some embodiments, each robotic manipulator is a movable arm that is capable of carrying tools in both horizontal and vertical planes i.e. in x-y-z planes. One tool contemplated is a pipetting tool. A robotic manipulator uses the pipetting tool to pick up liquid from a defined location on the work surface and then dispense the liquid at a different location. The pipetting tool can also be used to mix liquids by repeatedly picking up and ejecting the liquid i.e. "sip and spit" mixing. The robotic manipulator is also able to eject a disposable tip from the pipetting tool into a waste container, and then pick up a fresh tip from the appropriate station on the work surface.

In preferred embodiments, the pipetting tool is connected to one or more fluid reservoirs that contain some of the various buffers and reagents needed in bulk for the SELEX process. A computer controlled valve determines which solution is dispensed by the pipetting tool. The pipetting tool is further able to eject liquid at desired locations on the work surface without the outside of the tip coming in contact with liquid already present at that location. This greatly reduces the possibility of the pipette tip becoming contaminated at each liquid dispensing step, and reduces the number of pipette tip changes that must be made during the automated SELEX process.

In some embodiments, tips that are used at certain steps of the automated SELEX process can be reused. For example, a tip can be reused if it is used in each cycle of the SELEX process to dispense the same reagent. The tip can be rinsed after each use at a rinse station, and then stored in a rack on the work surface until it is needed again. Reusing tips in this way can drastically reduce the number of tips used during the automated SELEX process.

In preferred embodiments, a vacuum aspiration system is also attached to a separate robotic manipulator. This system uses a fine needle connected to a vacuum source to withdraw liquid from desired locations on the work surface without immersing the needle in that liquid. In embodiments where the pipetting tool and the vacuum aspirator are associated with separate robotic manipulators, the pipetting tool and the aspiration system can work simultaneously at different locations on the work surface.

In preferred embodiments, a robotic manipulator is also capable of moving objects to and from defined locations on the work surface. Such objects include lids for multi-well plates, and also the various pieces of apparatus used in the embodiments outlined below. In one embodiment of the invention, the robotic manipulator uses a "gripper" to mechanically grasp objects. Such a gripper is shown in FIG. 16. In other embodiments, the vacuum aspiration system described above is also used to power a suction cup that can attach to the object to be moved. For example, the fine needle described above can pick up a suction cup, apply a vacuum to the cup, pick up an object using the suction cup, move the object to a new location, release the object at the new location by releasing the vacuum, then deposit the suction cup at a storage location on the work surface.

Suitable robotic systems contemplated in the invention include the MultiPROBE™ system (Packard), the Biomek 200™ (Beckman Instruments) and the Tecan™ (Cavro). In the embodiment depicted in FIGS. 7–10, the system uses three robotic manipulators: one carries the pipetting tool, one carries a vacuum aspirator, and one carries the fluorometry cover (see below).

In its most basic embodiment, the automated SELEX process method involves:

(a) contacting a candidate mixture of nucleic acid ligands in a containment vessel with a target molecule that is associated with a solid support;

(b) incubating the candidate mixture and the solid support in the containment vessel at a predetermined temperature to allow candidate nucleic acid ligands to interact with the target;

(c) partitioning the solid support with bound target and associated nucleic acid ligands away from the candidate mixture;

(d) optionally washing the solid support under predetermined conditions to remove nucleic acid that are associated non-specifically with the solid support or the containment vessel;

(e) releasing from the solid support the nucleic acid ligands that interact specifically with the target;

(f) amplifying, purifying and quantifying the released nucleic acid ligands;

(g) repeating steps (a)–(f) a predetermined number of times; and (h) isolating the resulting nucleic acid ligands.

Steps (a)–(g) are performed automatically by the computer-controlled robotic manipulator. The computer also measures and stores information about the progress of the automated SELEX process procedure, including the amount of nucleic acid ligand eluted from the target molecule prior to each amplification step. The computer also controls the various heating and cooling steps required for the automated SELEX process. In preferred embodiments, the work surface comprises a single work station where the individual SELEX reactions take place. This station comprises heating and cooling means controlled by the computer in order to incubate the reaction mixtures at the required temperatures. One suitable heating and cooling means is a Peltier element. The work station preferably also comprises a shaking mechanism to insure that SELEX reaction components are adequately mixed. The work surface also comprises stations in which the enzymes necessary for SELEX are stored under refrigeration, stations where wash solutions and buffers are stored, stations where tools and apparatus are stored, stations where tools and apparatus may be rinsed, and stations where pipette tips and reagents are discarded. The work surface may also comprise stations for archival storage of small aliquots of the SELEX reaction mixtures. These mixtures may be automatically removed from the work station by the pipetting tool at selected times for later analysis. The work surface may also comprise reagent preparation stations where the robotic manipulator prepares batches of enzyme reagent solutions in preparation vials immediately prior to use.

In other embodiments, the work surface comprises more than one work station. In this way, it is possible to perform the individual steps of the automated SELEX process asynchronously. For example, while a first set of candidate nucleic acid ligands is being amplified on a first work station of step (f), another set from a different experiment may be contacted with the support-bound target molecule of step (b) on a different work station. Using multiple work stations minimizes the idle time of the robotic manipulator. FIG. 14 illustrates one embodiment of the work surface comprising a central module (a shaker for holding a microtiter plate, and heating/cooling means), a thermal cycler (capable of performing PCR), and reagent and tip racks.

In still other embodiments, the individual steps of the automated SELEX process are carried out at discrete work stations rather than at a single multi-functional work station. In these embodiments, the solutions of candidate nucleic acid mixtures are transferred from one work station to another by the robotic manipulator. Separate work stations may be provided for heating and cooling the reaction mixtures.

In preferred embodiments, the individual steps of the automated SELEX process are carried out in a containment vessel that is arranged in an array format. This allows many different SELEX reactions—using different targets or different reaction conditions—to take place simultaneously on a single work station. For example, in some embodiments the individual steps may be performed in the wells of microtitre plates, such as Immulon 1 plates. In other embodiments, an array of small plastic tubes is used. Typical tube arrays comprise 96 0.5 ml round-bottomed, thin-walled polypropylene tubes laid out in a 8×12 format. Arrays can be covered during the heating and cooling steps to prevent liquid loss through evaporation, and also to prevent contamination. Any variety of lids, including heated lids, can be placed over the arrays by the robotic manipulator during these times. Furthermore, arrays allow the use of multipipettor devices, which can greatly reduce the number of pipetting steps required. For the purposes of this specification, the term "well" will be used to refer to an individual containment vessel in any array format.

Solid supports suitable for attaching target molecules are well known in the art. Any solid support to which a target molecule can be attached, either covalently or non-covalently, is contemplated by the present invention. Covalent attachment of molecules to solid supports is well known in the art, and can be achieved using a wide variety of derivatization chemistries. Non-covalent attachment of targets can depend on hydrophobic interactions; alternatively, the solid support can be coated with streptavidin which will bind strongly to a target molecule that is conjugated to biotin. In preferred embodiments, target molecules are conjugated to solid support using a benzophenone-based crosslinker. For example, the succinimdyl ester of 4-benzoylbenzoic acid can be coupled to paramagnetic beads functionalized with primary amino groups. When the resulting beads are mixed with target protein and irradiated with 360 nm light, the benzophenone is photoactivated and covalently attaches to the protein. Examples 7, 8, and 9 below details the synthesis and use of benzophenone-labeled paramagnetic beads.

In particularly preferred embodiments, the solid support is a paramagnetic bead. When target molecules are attached to paramagnetic beads, complexes of target molecules and nucleic acid ligands can be rapidly partitioned from the candidate mixture by the application of a magnetic field to the wells. In preferred embodiments, the magnetic field is applied by an array of electromagnets adjacent to the walls of each well; when the electromagnets are activated by the computer, paramagnetic target beads are held to the sides of the wells. The magnets can either be an integral part of the work station, or they can be attached to a cover that is lowered over the work station by the robotic manipulator. In this latter embodiment, the magnetic separator cover allows the magnets to be placed adjacent to the wells without blocking access to the wells themselves. In this way, the wells are accessible by the pipetting and aspirating units when the cover is in place. Following magnet activation, liquid can be aspirated from the wells, followed by the addition of wash solutions. When the electromagnets are deactivated, or when the cover is removed, the beads become resuspended in the solution. The magnetic separator cover can be stored on the work surface. In other embodiments, the magnets in the separator cover are permanent magnets. In this case, withdrawing the cover removes the influence of the magnets, and allows the beads to go into suspension.

In still further embodiments, the magnets used for bead separation are attached to a series of bars that can slide between adjacent rows of wells. Each bar has magnets regularly spaced along its length, such that when the bar is fully inserted between the wells, each well is adjacent to at least one magnet. For example, an 8×12 array of wells would have 8 magnet bars, each bar with 12 magnets. In this embodiment, bead separation is achieved by inserting the bars between the wells; bead release is accomplished by withdrawing the bars from between the wells. The array of bars can be moved by a computer-controlled stepper motor. FIG. 16 illustrates a work surface that uses such a bar array.

The paramagnetic target beads used in the above embodiments are preferably stored on the work surface in an array format that mirrors the layout of the array format on the work station. The bead storage array is preferably cooled, and agitated to insure that the beads remain in suspension before use.

Beads can be completely removed from the wells of the work station using a second array of magnets. In preferred embodiments, this second array comprises an array of electromagnets mounted on a cover that can be placed by the robotic manipulator over the surface of the individual wells on the work station. The electromagnets on this bead removal cover are shaped so that they project into the liquid in the wells. When the electromagnets are activated, the beads are attracted to them. By then withdrawing the bead removal cover away from the wells, the beads can be efficiently removed from the work station. The beads can either be discarded, or can be deposited back in the bead storage array for use in the next cycle of automated SELEX. The bead removal cover can then be washed at a wash station on the work surface prior to the next bead removal step.

In a typical embodiment involving paramagnetic beads, the automated SELEX process begins when the pipetting tool dispenses aliquots of the beads—with their bound target—to the individual wells of a microtitre plate located on the work station. Each well already contains an aliquot of a candidate mixture of nucleic acid ligands previously dispensed by the robotic manipulator. After dispensing the beads, the robot optionally "sips and spits" the contents of each well up and down several times to facilitate thorough mixing. The microtitre plate is then incubated at a preselected temperature on the work station in order to allow nucleic acid ligands in the candidate mixture to bind to the bead-bound target molecule. Agitation of the plate insures that the beads remain in suspension. After incubation for a suitable time, the magnetic separator cover is placed over the microtitre plate by the robotic manipulator. The beads are then held to the sides of the wells, and the aspirator tool removes the solution containing unbound candidate nucleic acids from the wells. A washing solution, such as a low salt solution, can then be dispensed into each well by the pipetting tool. The beads are released from the side of the wells by withdrawing the magnetic separator cover or deactivating the electromagnets, then resuspended in the wash solution by agitation and "sip and spit" mixing. The magnetic separator cover is placed over the plate again, and the wash solution is aspirated. This wash loop can be repeated for a pre-selected number of cycles. At the end of the wash loop, the beads are held by the magnets to the sides of the empty wells.

The beads can then be resuspended in a solution designed to elute the nucleic acid ligands from the target molecule, such as $dH_2O$. The dissociation of nucleic acid ligand from target can also be achieved by heating the beads to a high temperature on the work station. After dissociation of the nucleic acid ligands from the bead-bound target, the pipetting tool can dispense into the wells the enzyme and buffer components necessary to perform amplification of the candidate nucleic acid ligands. After amplification, purification and quantification (see below), a predetermined amount of the amplified candidate mixture can then used in the next cycle of the automated SELEX process. At any point during the cycles, the pipetting tool can remove an aliquot of the candidate mixture and store it in an archive plate for later characterization. Furthermore, during incubation periods, the pipetting tool can prepare reaction mixtures for other steps in the SELEX process.

As described above, the preferred embodiments of the automated SELEX process method and apparatus use microtitre plates and magnetic beads to achieve selection. However, any other method for partitioning bound nucleic acid ligands from unbound is contemplated in the invention. For example, in some embodiments, the target molecule is coupled directly to the surface of the microtitre plate. Suitable methods for coupling in this manner are well known in the art.

In other embodiments, the target molecule is coupled to affinity separation columns known in the art. The robotic device would dispense the candidate mixture into such a column, and the bound nucleic acid ligands could be eluted into the wells of a microtitre plate after suitable washing steps.

In still other embodiments, the solid support used in the automated SELEX process method is a surface plasmon resonance (SPR) sensor chip. The use of SPR sensor chips in the isolation of nucleic acid ligands is described in WO 98/33941, entitled "Flow Cell SELEX," incorporated herein by reference in its entirety. In the Flow Cell SELEX method, a target molecule is coupled to the surface of a surface plasmon resonance sensor chip. The refractive index at the junction of the surface of the chip and the surrounding medium is extremely sensitive to material bound to the surface of the chip. In one embodiment of the present invention, a candidate mixture of nucleic acid ligands is passed over the chip by the robotic device, and the kinetics of the binding interaction between the chip-bound target and nucleic acid ligands is monitored by taking readings of the resonance signal from the chip. Such readings can be made using a device such as the BIACore 2000™ (BIACore, Inc.). Bound nucleic acid ligands can then be eluted from the chip; the kinetics of dissociation can be followed by measuring the resonance signal. In this way it is possible to program the computer that controls the automated SELEX process to automatically collect nucleic acid ligands which have a very fast association rate with the target of interest and a slow off rate. The collected nucleic acid ligands can then be amplified and the automated SELEX process cycle can begin again.

In still other embodiments, the solid support is a non-paramagnetic bead. Solutions can be removed from the wells containing such beads by aspirating the liquid through a hole in the well that is small enough to exclude the passage of the beads. For example, a vacuum manifold with a 0.2 $\mu$M filter could be used to partition 100 $\mu$M beads.

At the end of the automated SELEX process, the resulting nucleic acid ligands can be isolated from the automated SELEX process apparatus for sequence analysis and cloning.

Amplification of the Candidate Nucleic Acid Ligands

At the end of each binding and partitioning step in the automated SELEX process method, the candidate nucleic acid ligands must be amplified. In preferred embodiments, the amplification is achieved using the Polymerase Chain Reaction (PCR). As the candidate nucleic acid ligands in the automated SELEX process method preferably all have fixed 5' and 3' regions, primers that bind to these regions are used to facilitate PCR.

In embodiments that use target beads, the beads are removed from the wells before beginning the amplification procedure. When paramagnetic beads are used, this can be done using the magnetic removal system described above.

Candidate nucleic acid ligands can be single-stranded DNA molecules, double-stranded DNA molecules, single-stranded RNA molecules, or double-stranded RNA molecules. In order to amplify RNA nucleic acid ligands in a candidate mixture, it is necessary to first reverse transcribe the RNA to cDNA, then perform the PCR on the cDNA. This process, known as RT-PCR, can be carried out using the automated SELEX process method by dispensing the necessary enzymes, primers and buffers to the wells on the work station containing the eluted ligand. The resulting reaction mixtures are then first incubated on the work station at a temperature that promotes reverse transcription. After reverse transcription, the work station thermally-cycles the reaction mixtures to amplify the cDNA products. The amount of amplified product is then measured to give a value for the amount of candidate nucleic acid ligand eluted from the target (see below).

For RNA ligands, the amplified DNA molecules must be transcribed to regenerate the pool of candidate RNA ligands for the next cycle of automated SELEX. This can be achieved by using primers in the amplification step that contain sites that promote transcription, such as the T7 polymerase site. These primers become incorporated into the amplification product during the PCR step. Transcription from these sites can be achieved simply by dispensing the appropriate enzymes and buffer components into the amplified mixtures and then incubating at the appropriate temperature. A predetermined amount of the amplified mixture is then used in the next cycle of the automated SELEX process.

In some embodiments, the primers used for amplification of the DNA molecules (which molecules are either DNA ligands or cDNA formed by the reverse transcription of RNA ligands) are conjugated to a molecule useful for capture of the strand(s) into which the primer is incorporated during PCR. For example, the primer can be conjugated to biotin; products that have incorporated the biotin primer can be partitioned using streptavidin-conjugated solid supports, such as paramagnetic beads. Alternatively, the primer can bear a unique capture sequence, allowing paramagnetic beads conjugated to a complementary nucleic acid to partition PCR products that have incorporated the primer. Furthermore, by incorporating the capture molecule into only one primer and then partitioning under denaturing conditions, it is possible to perform strand separation. For example, if the capture molecule is biotin, then adding streptavidin-conjugated paramagnetic beads to the PCR products under denaturing conditions will lead to the capture of single-stranded nucleic acid that has incorporated the primer. In this way, the sense strand (the strand that actually forms a DNA ligand, or is the template for transcription of an RNA ligand) and the antisense strand can be partitioned from one another as required.

Parasite Formation During the Automated SELEX Process

After multiple rounds of the automated SELEX process, the dominant nucleic acid product occasionally comprises high molecular weight nucleic acids without ligand activity. While not wishing to be bound by any particular theory, it is believed that these nucleic acid species—which are termed "parasites"—result from rare mispriming events that occur during PCR. These mispriming events are believed to occur when rare candidate nucleic acid ligands contain a sequence in their random regions that is complementary in sequence to the 3' fixed sequence. If the 3' fixed sequence folds back over this complementary sequence in the random region, a self-priming intramolecular duplex may form. This structure can be extended by Taq polymerase to form a longer product during PCR amplification. Alternatively, the 3' fixed sequence of another candidate nucleic acid ligand can form an intermolecular duplex with the complementary sequence in the random region, and the 3' end of the former candidate nucleic acid can be extended by Taq polymerase to form a longer product. A series of either of these events will produce parasites with a variable number of repeats. Once these parasites have formed, they will anneal promiscuously with other nucleic acids, including the correct products, leading to the formation of ever-larger parasites through 3' end extension. As parasites grow, they contain more and more primer binding sites, allowing them to be efficiently amplified during the PCR process at the expense of bonafide nucleic acid ligands for primer. In the most extreme cases, nucleic acid ligand products are sometimes eliminated from the candidate mixture of nucleic acid ligands that contains a parasite.

Parasites most commonly form and grow during the later cycles of PCR where the concentration of free primer no longer exceeds the concentration of the product. Once a parasite has formed in an automated SELEX experiment, it contaminates the entire laboratory environment. Whenever automated SELEX experiments are performed using the same primer set, the parasite is efficiently amplified, grows by promiscuous annealing as described above, and quickly overwhelms the SELEX process.

Rather than being restricted to the SELEX process, parasites can be expected to arise in any type of automated nucleic acid selection process in which nucleic acid amplification is employed. For example, parasite formation has been described by Cox et al., Biotechnol. Prog. 14:845–850 (1998), incorporated herein by reference in its entirety, using an automated nucleic acid selection process in which amplification of the candidate nucleic acid mixture is performed by isothermal amplication, rather than PCR. Marshall & Ellington, J. Mol. Evol. 49: 656–663(1999), incorporated herein by reference in its entirety, report that once the isothermal amplification parasite has formed, it will dominate all subsequent reactions using the same primers. Cleaning of equipment and reagents, halting experiments for 4 months, and even moving to different rooms within the same facility could not prevent this parasite from dominating subsequent amplification reactions.

Cox et al., report that the initial formation of the parasite could be prevented by using PCR rather than isothermal amplification. However, it must be noted that the automated selection process performed by Cox et al., was not equivalent to the SELEX process because it was aimed at obtaining nucleic acids that could hybridize to an oligo dT target through Watson-Crick base-pairing. Because selection for nucleic acids that can hybridize to a nucleic acid target is a far simpler and more efficient process than the SELEX process, Cox et al., were able to use only a very few cycles of the PCR process to amplify their candidate nucleic acids. The low number of cycles used meant that parasites never had a chance to form. By contrast, it is necessary to use many more cycles of the PCR to efficiently amplify candidate nucleic acid mixtures in the SELEX processes described herein, thereby increasing the likelihood of parasite formation in those PCR reaction mixtures.

It is possible to delay or prevent parasites from dominating the automated SELEX process by size fractionating PCR products using acrylamide gel electrophoresis before beginning the next round of the SELEX process. However, it is extremely cumbersome to automate this gel electrophoresis step because of the difficulties well known in the art in automating gel loading and DNA product excision. Moreover, because gel electrophoresis is time-consuming, it would be the rate-limiting step in any automated SELEX process that employs it. Accordingly, it is an object of the present invention to provide nucleic acid amplification procedures that prevent the formation of parasites during the automated nucleic acid selection procedures that rely on nuleic acid amplification, particularly during the automated SELEX process.

As mentioned above, parasites commonly form and grow during the later cycles of PCR when most primer has been incorporated. In some embodiments of the automated SELEX process, parasite formation and/or growth can be prevented, or at least delayed until later rounds of the automated SELEX process, by monitoring each PCR reaction, and then terminating individual reactions once they have progressed to the desired degree of completion. The fluorescence methods provided below in the section entitled "Calculation of Amount of Eluted Nucleic Acid Ligand in Each Amplification Mixture" allow each PCR reaction to be monitored in real time to determine how much primer has been incorporated at a particular time point. In one such embodiment, each PCR reaction has independent thermal control. For example, if the PCR reactions of parallel automated SELEX processes are carried out on a microtiter plate, then each well of the plate can be associated with a separate Peltier element. Individual PCR reactions can be terminated by cooling to 4° C., while other reactions in the microtitre plate continue to undergo thermal cycling. In alternative embodiments, individual PCR reactions can be terminated by the addition thereto of an inhibitor of PCR (such as EDTA) by the pipetting tool that is under control of the robotic manipulator.

In preferred embodiments, the likelihood that parasites will form is reduced by adding sequences with melting temperature (Tm) values lower than the PCR annealing temperature to the 5' termini of the PCR primers. At the annealing temperature, hybridization of these sequences to their complements is unstable, whereas the primers anneal to the fixed sequence regions of the candidate nucleic acids. These unstable sequences that are added to the 5' end of primers are referred to as "tails." For example, PCR can be performed with one primer linked to a tail sequence ATATATAT, and the other linked to the tail sequence TTTTTTTT. The correct PCR product will have ATATATAT on the 3' terminus of one strand and AAAAAAAA on the 3' terminus of the other strand. At a typical PCR annealing temperature of 60° C., the tail sequences AAAAAAAA and ATATATAT will not anneal intra- or intermolecularly to the random regions of candidate nucleic acid ligands that fortuitously contain the complements of those sequences. It will be recognized by those skilled in the art that other sequences with low Tm may also be used.

If the random region contains a sequence complementary both to the primer and the tail, then there is a chance that an intramolecular or intermolecular duplex may form during the PCR annealing and extension step. The primer and its complement will form a duplex, but the 3' end of the duplex (at which extension must occur) will be unstable at the PCR annealing temperature because of the presence of the tail sequence. Because polymerase absolutely requires a base-paired 3' terminal nucleotide in order to begin extension, polymerase extension of this structure will be an extremely rare event.

Figure 11:
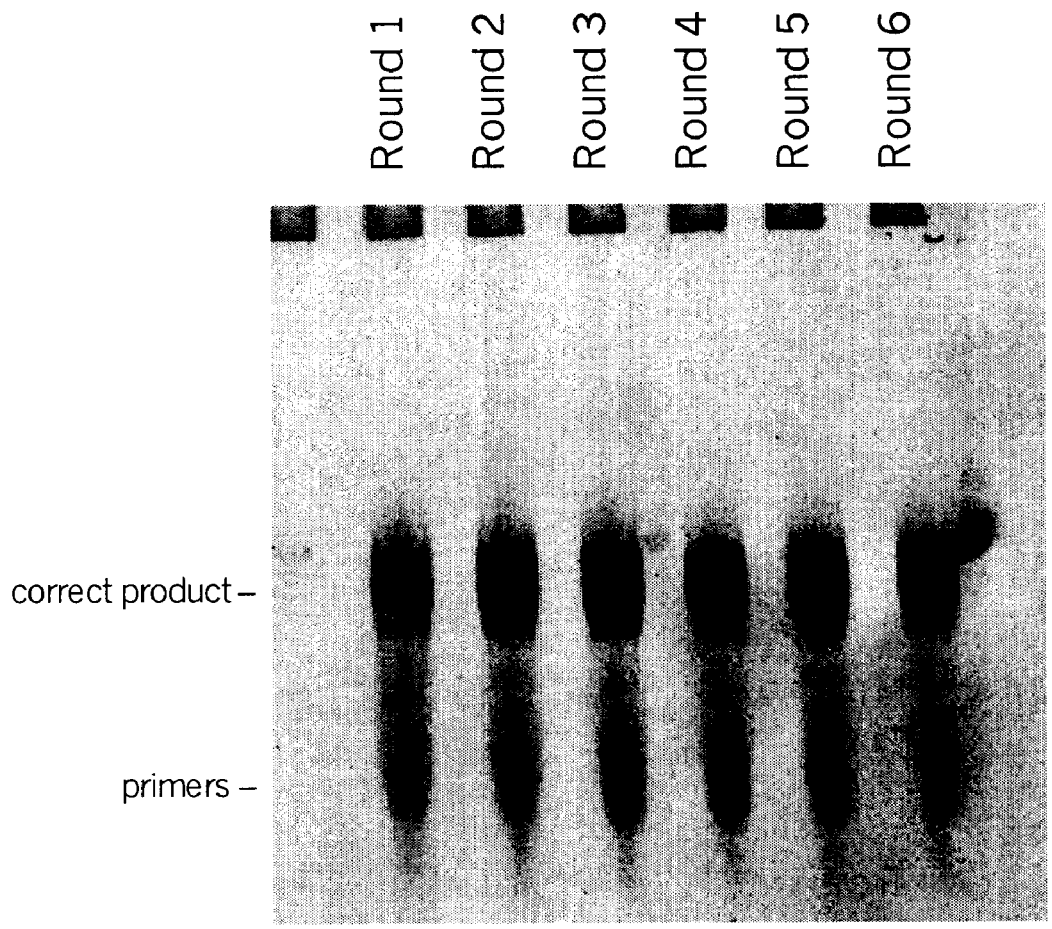
FIG. 11 shows an example of a SELEX process in which using PCR primers with unstable 5' tail sequences leads to the formation of product of correct size.

Example 4 and FIG. 11 illustrates one primer set that can be used in this embodiment, and demonstrates that no high molecular weight DNA arises when these primers are used in 6 rounds of the amplification process used during the SELEX process, each round involving 40 cycles of the PCR process.

In preferred embodiments, the initial candidate mixture also has unstable tail sequences at its 5' and 3' ends to minimize the chance that parasites form during the first PCR cycle. For example, if the primers described above are used, then the initial candidate mixture could have the sequence ATATATAT at its 5' end, and the sequence AAAAAAAA at its 3' end.

Example 5 provides example sequences of tailed candidate nucleic acid mixtures and primers with a variety of Tm values. The higher the Tm value, the higher the temperature at which the annealing and extension steps of the PCR process can be carried out. The data indicate that parasites form more quickly with higher Tm tailed primers than with lower Tm tailed primers when 40 cycles of PCR are performed at each round of the automated SELEX process. This result at first seems to be unexpected because it would be thought that the tails further decrease in stability as the annealing temperature increases. Without being limited to a single theory, it is believed that when primers with higher Tm values are used, PCR is completed within a fewer number of cycles than when primers with lower Tm values are used. As a result, some reactions are completed after 20 cycles, and so continue to cycle unproductively for 20 further cycles, and, as mentioned above, parasite formation is believed to occur more frequently during unproductive PCR cycles than during cycles where free primer is still available. Thus, it is possible that the parasites form during these unproductive cycles, even in the presence of very unstable tails. In order to circumvent this effect, in preferred embodiments of the invention the number of PCR cycles is optimized for each tailed primer set, such that the number of unproductive PCR cycles is minimized.

Even when parasites do form in the presence of tailed primers, they grow in size and frequency much more slowly during the automated SELEX process than when untailed primers are used for amplification. Rather than very quickly dominating within the first round of the automated SELEX process, the parasites that the arise in tailed primer PCR reactions merely become increasingly prevalent over the last 4 to 6 rounds of selection. This can be seen by comparing the untailed N11 gel and the tailed N11, N17, and N18 gels in Example 5 and FIG. 12. The untailed N11 gel shows a smear of high molecular weight DNA starting at the very top of the gel at Round 2. By contrast, the parasites in the tailed primer experiments in FIG. 12 gradually form a more discrete "ladder" pattern over several rounds of the SELEX process. Parasites that arise in PCR reactions with tailed primers can still anneal to other DNA molecules—including the correct products—but extension from the 3' end of the parasite is rare because of the presence of the unstable tail. Parasite growth in the presence of tailed primers is therefore the result of a series of rare events, so it occurs much more slowly than in untailed PCR reactions.

As noted above, once a parasite has formed using untailed primers, that same parasite contaminates the entire laboratory environment, and quickly dominates all subsequent experiments using the same primer set. By contrast, the rare parasites that arise when tailed primers are used do not dominate other experiments because, again, they grow very slowly due to their 3' unstable tails. Example 6 and FIG. 13 shows that when total DNA from a untailed primer PCR experiment in which a parasite formed is used to "contaminate" a tailed primer PCR reaction, that parasite will still not dominate the new PCR reaction.

In some embodiments, polymerase(s) that lack 3' to 5' exonuclease activity are used to amplify candidate nucleic acids in the presence of tailed primers. Using polymerases that lack 3' to 5' exonuclease activity maximizes the likelihood that the unstable tail sequences of candidate mixture nucleic acids will remain intact during the amplification process. One suitable enzyme that lacks exonuclease activity is Taq polymerase.

In another series of embodiments, parasite formation is prevented by selectively depleting the candidate mixture of those nucleic acids whose random region fortuitously contains the complement of the 3' fixed region sequence. As discussed above, such nucleic acids are believed to be reponsible for the generation of parasites. Preferably, depletion is achieved by preparing solid supports that are conjugated to nucleic acid primers comprising sequence from the 3' fixed region. The candidate mixture is then contacted with the solid support, and nucleic acids that contain the complement of the 3' fixed region in their random regions bind to the solid support-bound primer.

In some embodiments of the depletion method, the solid support is a column; a candidate mixture can be run through the column under hybridizing conditions, and the column eluant used as the candidate nucleic acid mixture for the automated SELEX process. In further embodiments, the solid support comprises paramagnetic beads; a candidate mixture can be mixed with the beads under hybridizing conditions, and the nucleic acids that remain in solution can be used as the candidate nucleic acid mixture for the automated SELEX process. The depletion procedure can be carried out during each round of the automated SELEX process, preferably immediately before the PCR step. Alternatively, the depletion process may be performed just once before the initiation of the automated SELEX process. For example, following synthesis of a candidate nucleic acid mixture by an automated nucleic acid synthesizer, the candidate mixture can be depleted of parasite-generating nucleic acids and the resulting depleted candidate nucleic acid mixture can be frozen in aliquots for later use in the automated SELEX process. In addition, the parasite depletion process can be combined with the tailed primer process in order to reduce dramatically the likelihood of parasite formation during the automated SELEX process.

It will be appreciated that use of the tailed primers and the parasite-depleting solid supports described herein need not be restricted to the automated SELEX process. The tailed primers can be used in the conventional "manual" SELEX process, thereby avoiding the need to size-fractionate PCR products before beginning the next round of the SELEX process.

It will further be understood by those skilled in the art that the methods of the instant invention for the prevention of parasite formation during nucleic acid amplification will also have great utility in procedures other than the automated SELEX process. In general, parasite formation can be expected to occur in any amplification procedure in which there is a possibility that the 3' terminal region of a nucleic acid that is to be amplified can anneal to another sequence (other than to a primer which is specifically designed to hybridize thereto) either intramolecularly or intermolecularly, and thereby serve as a primer for extension by a polymerase. As outlined above, parasite formation is especially likely to occur in molecular evolution procedures where a population of nucleic acids with at least partially randomized sequences is selected for a certain property, amplified using fixed terminal sequences, and the resulting amplified mixture used, without size-fractionation, to initiate another round of selection. Automated molecular evolution procedures are especially likely to generate parasites because they are frequently performed without size-fractionation due to the well-characterized difficulties in automating this process.

One example of a molecular evolution method likely to suffer from parasite formation when performed without size-fractionation of amplification products is the Systematic Polypeptide Evolution by Reverse Translation method, described in U.S. Pat. Nos. 6,194,550 and 5,843,701, each of which is entitled "Systematic Polypeptide Evolution by Reverse Translation," and U.S. Pat. No. 5,658,754, entitled "Cell-Free Synthesis and Isolation of Novel Genes and Polypeptides." A nucleic acid pool is used to evolve a polypeptide ligand with affinity for a particular target molecule. Specifically, a candidate mixture of translatable mRNA is prepared, wherein each mRNA comprises (from 5' to 3') the following features: a 5' fixed sequence region, a ribosome binding site, a translation initiation codon, a region of at least partially randomized sequence with coding potential, and a 3' fixed sequence region. The mRNA is translated in vitro in such a way that each translated mRNA remains associated—either directly or indirectly—with the polypeptide that it encodes, thereby forming a mRNA•polypeptide copolymer. This may be done by using a candidate mixture of translatable mRNA molecules in which each mRNA molecule has a chemical modification that allows the formation a covalent bond or a tight affinity interaction with a portion of the translated polypeptide i.e., a direct association. Alternatively, ribosome complexes can be isolated, in which mRNA and nascent polypeptide are stably associated with the ribosome i.e., an indirect association. Copolymers are partitioned on the basis of the affinity of the polypeptide component of the copolymer for the target molecule.

Following partitioning, the mRNA component of partitioned copolymer is then amplified, preferably according to the following method. First, full-length cDNA copies of the mRNA molecules are made using reverse transcriptase primed with an oligomer complementary to the 3' fixed sequence region. The resultant cDNAs are amplified by the Polymerase Chain Reaction, employing a primer containing a promoter sequence as well as a primer complementary to the 5' fixed sequence region of the selected RNAs. Double-stranded products of this amplification process are then transcribed in vitro. Transcripts are used in the next selection/amplification cycle.

Selection and amplification can proceed until a polypeptide with the desired affinity is obtained; the mRNA component of the mRNA•polypeptide copolymer can then be sequenced to determine the amino acid sequence of the polypeptide.

As in the SELEX process, this process for synthesis and isolation of novel genes and polypeptides involves the amplification of nucleic acids that comprise random sequence regions flanked by fixed sequence regions. During amplification of cDNA in this method, fixed 3' terminal sequences may fortuitously anneal intra- or intermolecularly with sequences in the randomized region(s) of the cDNA. Extension of these intra- or intermolecular duplexes will lead to parasite formation; if size-fractionation of the PCR reaction products is not performed, then the parasite may grow and be propagated as described above, ultimately leading to the disruption, or even failure, of the process. Similarly, during reverse transcription the fixed 3' terminal sequences of a mRNA may fortuitously anneal intra- or intermolecularly with sequences in the randomized region(s) of the mRNA. Extension of such RNA duplexes may lead to parasite formation, and those parasites would be amplified by the subsequent PCR process. The methods of the instant invention can be used to prevent such parasite formation during embodiments of the SPERT procedure that lack size-fractionation procedures e.g., during automated embodiments. For example, the 5' and 3' ends of the candidate mixture mRNA and/or the 5' ends of the primers used for PCR amplification of the cDNA can be attached to tail sequences that have a Tm below the annealing temperature used for PCR amplification. As in the SELEX embodiments described above, this will result in the creation of unstable 3' ends in candidate mixture during PCR amplification, thereby preventing intermolecular or intramolecular self-priming by candidate nucleic acids. Alternatively, candidate mixture mRNA (or the DNA/cDNA that is transcribed to yield that mRNA) may be depleted of those molecules in which the 3' fixed sequence region fortuitously complements a sequence found in the randomized region e.g., by contacting candidate nucleic acids with solid support-bound primers comprising sequence from the 3' fixed sequence region, and then discarding those nucleic acids that anneal to the primer.

Purification of RNA Ligands from Amplification Mixtures

In some embodiments, amplified RNA ligands are purified from their DNA templates before beginning the next cycle of the automated SELEX process. This can be done using a second set of paramagnetic beads to which primers complementary to the 3' fixed region of the RNA ligands are attached. When these primer beads are added to the transcribed amplification mixture, the newly transcribed full length RNA ligands hybridize to the bead-bound primer, whereas the amplified double-stranded DNA molecules remain in solution. The beads can be separated from the reaction mixture by applying a magnetic field to the wells and aspirating the liquid in the wells, as described above. The beads can then be washed in the appropriate buffer at a preselected temperature, and then the RNA ligands may be eluted from the beads by heating in an elution buffer (typically $dH_2O$). Finally, the beads may be removed from the wells on the work station, as described above to leave only a solution of candidate RNA ligands remaining in the wells. This point marks the completion of one cycle of the automated SELEX procedure.

The amount of primer bead added determines the amount of RNA ligand that is retained in the wells. Therefore, the amount of RNA ligand that is used in the next cycle of the automated SELEX procedure can be controlled by varying the amount of primer bead that is added to the amplification mixture. The amount of RNA ligand that is to be used can be determined through quantitation of the amount of PCR product (see below).

Calculation of the Amount of Eluted Nucleic Acid Ligand in Each Amplification Mixture In certain embodiments, it may be important to measure the amount of candidate nucleic acid ligand eluted from the target before beginning the next cycle of the automated SELEX process. Such measurements yield information about the efficiency and progress of the selection process. The measurement of eluted nucleic acid ligand—which serves as template for the amplification reaction—can be calculated based on measurements of the amount of amplification product arising out of each PCR reaction.

In some embodiments, the automated SELEX process method uses a novel system for the automated real-time quantitation of PCR products during amplification. This, in turn, permits the progress of the selection experiment to be monitored in real time during the automated SELEX process. In preferred embodiments, the automated SELEX process method uses a fluorophore/quencher pair primer system. This system is used to calculate automatically the amount of eluted nucleic acid ligand introduced into the reaction mixture by measuring the fluorescence emission of the amplified mixture. In one such embodiment of the invention, the PCR reaction is carried out using primers that have a short hairpin region attached to their 5' ends. The stem of the hairpin has a fluorophore attached to one side and a quencher attached on the other side opposite the fluorophore. The quencher and the fluorophore are located close enough to one another in the stem that efficient energy transfer occurs, and so very little fluorescent signal is generated upon excitation of the fluorophore. Hence, free primers in solution generate a low fluorescence signal. Examples of such primers are described in Example 3. During the PCR process, each primer binds to the appropriate sequence at the annealing step, and polymerase extends the 3' end of the primer to form new template. At the next cycle of the PCR process, polymerase copies the hairpin sequence of this new template to form double stranded DNA, and in doing so the polymerase disrupts the hairpin. As a result, the distance between the quencher and the fluorophore increases, and the efficiency of quenching energy transfer drops dramatically. An incorporated primer therefore has a much higher fluorescence emission signal than an unincorporated primer. By monitoring the fluorescence signal as a function of the PCR cycle number, PCR reaction kinetics can be monitored in real time. In this way, the amount of candidate nucleic acid ligand eluted from target in each reaction can be quantitated. This information in turn is used to follow the progress of the selection process.

In preferred embodiments, the amount of PCR product is measured using a fluorescent dye that preferentially binds to double stranded DNA (dsDNA). One suitable dye is SYBR Green I, available from Molecular Probes, Inc. The fluorescence signal of this dye undergoes a huge enhancement upon binding to dsDNA, allowing dsDNA to be detected in real time within the PCR reaction mixture, without fluorescent signal contribution from the single stranded primers. Methods for the use of SYBR Green in quantitative PCR applications are described in Schneeberger, et al., PCR Meth. Appl. 4: 234 (1995), incorporated herein by reference in its entirety.

In some embodiments, one or both of the primers used for the quantitative PCR bears a capture molecule. This enables the PCR products to be partitioned from the reaction mixture by the addition of solid supports that can bind the capture molecule. For example, if the capture molecule is biotin, then streptavidin-conjugated paramagnetic beads can be used to partition the PCR products that have incorporated the primer. As described above, it is possible to use the biotin-conjugated primer method to partition the individual strands of the PCR products from one another. This latter method also facilitates the removal of the quantitating dye in the embodiment described above, if removal is desired.

In other embodiments, the candidate nucleic acid ligand templates are quantitated using the TaqMan™ probe PCR system available from Roche Molecular Systems. Briefly, a TaqMan™ probe is an oligonucleotide with a sequence complementary to the template being detected, a fluorophore on the 5' end, and a quencher on the 3' end. The probe is added to a standard PCR reaction and anneals to the template between the primer binding sites during the annealing phase of each PCR cycle. During the extension phase, the probe is degraded by the 5'→3' exonuclease activity of Taq Polymerase, separating the fluorophore from the quencher and generating a signal. Before PCR begins, the probe is intact and the excitation energy of the fluorophore is non-radiatively transferred to the quencher. During PCR, as template is amplified, the probe is degraded and the amount of fluorescent signal generated is directly proportional to the amount of PCR product formed.

The current invention contemplates the use of fluorometry instruments that can monitor the fluorescence emission profile of the reaction mixture(s) on the work station during thermal-cycling. Suitable instruments contemplated comprise a source for excitation of the fluorophore, such as a laser, and means for measuring the fluorescence emission from the reaction mixture, such as a Charge Coupled Device (CCD) camera. Appropriate filters are used to select the correct excitation and emission wavelengths. Especially preferred embodiments use a fluorometry instrument mounted on an optically-transparent cover that can be placed over the wells on the work station by the robotic manipulator. When placed over the wells and then covered with a light shield, this fluorometry cover can capture an image of the entire array at pre-selected intervals. The computer interprets this image to calculate values for the amount of amplified product in each well at that time. At the end of the amplification step, the robotic manipulator removes the light shield and fluorometry cover and returns them to a storage station on the work surface.

In preferred embodiments, measurements of PCR product quantity are used to determine a value for the amount of eluted nucleic acid ligand introduced as template into the amplification reaction mixture. This can be done by comparing the amount of amplified product with values stored in the computer that were previously obtained from known concentrations of template amplified under the same conditions. In other embodiments, the automated SELEX process apparatus automatically performs control PCR experiments with known quantities of template in parallel with the candidate nucleic acid amplification reactions. This allows the computer to re-calibrate the fluorescence detection means internally after each amplification step of the automated SELEX process.

The value for the amount of candidate nucleic acid ligand eluted from the target is used by the computer to make optimizing adjustments to any of the steps of the automated SELEX process method that follow. For example, the computer can change the selection conditions in order to increase or decrease the stringency of the interaction between the candidate nucleic acid ligands and the target. The computer can also calculate how much of the nucleic acid ligand mixture and/or target bead should be used in the next SELEX cycle. In embodiments using primer beads (above), the computer uses this information to determine the amount of primer bead suspension to be added to each well on the work station. Similarly, the computer can change the conditions under which the candidate nucleic acid ligands are amplified. All of this can be optimized automatically without the need for operator intervention.

The methods provided herein allow dynamic, real-time quantitation of PCR product in each parallel PCR reaction. As discussed above, this information can be used to determine when an individual PCR reaction has incorporated all of the free primer initially added. Reactions identified in this way can be terminated according to the methods described above in order to prevent the unproductive cycling that can lead to formation of parasites.

Automated PhotoSELEX

In some embodiments of the invention, the automated SELEX process is used to generate nucleic acid ligands that undergo photochemical crosslinking to their targets. Photocrosslinkable nucleic acid ligands, and methods for their production, termed the photoSELEX methods, are described in great detail in U.S. patent application Ser. No. 08/123,935, filed Sep. 17, 1993, and U.S. patent application Ser. No. 08/443,959 filed May 18, 1995, both entitled "Photoselection of Nucleic Acid Ligands," and both now abandoned, and in U.S. Pat. No. 5,763,177, U.S. Pat. No. 6,001,577, WO 95/08003, U.S. Pat. No. 6,291,184, U.S. Pat. No. 6,458,539, and U.S. patent application Ser. No. 09/723,718, filed Nov. 28, 2000, each of which is entitled "Systematic Evolution of Nucleic Acid Ligands by Exponential Enrichment: Photoselection of Nucleic Acid Ligands and Solution SELEX." Any modified nucleotide residue that is capable of photocrosslinking (or chemically reacting) with a target molecule, such as 5-BrdU, 5-BrdT, 5-IdU or other 5-modified nucleotides, can be incorporated into the candidate mixture and may be useful in this application. In preferred embodiments, the crosslinking occurs when 5-bromo-deoxyuracil (5-BrdU) or 5-bromo-deoxythymidine (5-BrdT) residues incorporated into a nucleic acid ligand are irradiated with ultraviolet (UV) light. Photocrosslinkable nucleic acid ligands are useful because they enable assays in which very stringent (even denaturing) washes can be used to prevent non-specific interactions between targets and nucleic acid ligands.

Two embodiments are depicted graphically in FIGS. 14 and 15. In these embodiments, candidate mixtures of 5-BrdU or 5-BrdT-containing nucleic acid ligands 120 and 130 are dispensed to the individual wells of a microtiter plate located on the work station, along with target molecules 121 and 131 conjugated to paramagnetic beads 122 and 132. Following incubation of the reaction mixtures, the wells of the microtiter plate are irradiated with UV light to induce the formation of crosslinks 123 and 133 between the bead-bound target and candidate nucleic acid ligands that have bound to the target. In especially preferred embodiments, the UV light has a wavelength of 308 nm, with an intensity of around 500 mW/cm$^2$ to photo-activate the 5-BrdU present in the nucleic acid molecules within the pool. UV light sources can be either laser (monochromatic) or appropriately filtered lamp sources. The light source may reside on the work surface for direct irradiation; the robotic manipulator can either move the light source to the work station, or the microtiter plate can be moved to the light source. Alternatively, fiber optic light guides or mirrors, or a combination of fiber optics and mirrors, can be used to deliver the light from a source outside the work surface. The total amount of energy delivered to each sample well is individually controlled. In one embodiment of the invention, this control will be achieved using mechanical or liquid crystal shutters placed over the microtiter plate. Such shutters and appropriate lenses/filters will be placed in position via stepper motors and rails mounted above the central magnetic separation module. In another embodiment, the light will be shuttered at the source located off the station and delivered to each well via 96 fiber optic bundles. The fiber bundles can be delivered with a stepper motor and rail mount or by one of the robotic manipulators. Both shuttering methods allow for the simultaneous irradiation of all wells for individually prescribed times. In yet another embodiment, control of UW photo-activation light will be achieved by using a single fiber optic bundle carried by the robotic manipulator. Each well is irradiated separately, one after another, by moving the light bundle to a prescribed distance centered above a well for the desired length of time. The diameter of light from such a bundle will be ~7 mm, corresponding to the size of a single microtiter plate well.

Following washing of the target beads as described above, the bound nucleic acid ligands can be denatured. For protein targets, the target beads can then be treated with proteinase K to digest the target that has become covalently-linked to the nucleic acid ligands, thus releasing the nucleic acid ligands 124 and 134 from the beads. Amplification and quantitation of the candidate nucleic acid ligands can then proceed by any of the methods described elsewhere in the instant application. Two embodiments are described in detail below.

In one embodiment, depicted in FIG. 14, the released nucleic acid ligands 124 can be captured by paramagnetic beads 125 that are conjugated to a primer 126 capable of binding to the 3' fixed region of the ligands. The nucleic acids ligands anneal to this primer, and can then be quantitated by PCR as described above following the addition of a fluorophore (F)/quencher(Q)-conjugated primer 127 that binds to the 5' end of the nucleic acid ligand. During the PCR process, the primer that is conjugated to the beads is extended at its 3' end to yield a bead-bound antisense copy 128 of the nucleic acid ligand. If the beads are recovered after PCR, then this antisense copy 128 can serve as a template for the polymerization (in the presence of 5-BrdU or 5-BrdT and the appropriate primer, 5P7 in the illustration) of copies of the nucleic acid ligand 129. The bead-bound template can then be partitioned from the nascent nucleic acid ligands 129.

In another embodiment, depicted in FIG. 15, nucleic acid ligands 134 released from target beads by proteinase K digestion are captured by primer-conjugated paramagnetic beads 135 as described above, but are then eluted from the beads in NaOH. The free nucleic acid ligands 137 are then quantitated as described above using a primer pair comprising a fluorophore (F)/quencher (Q) conjugated primer 138 (named SF7-B) that has sequence from the 5' fixed region of the nucleic acid ligand and a primer 139 (named 3P7.1-B) that anneals to the 3' fixed region of the nucleic acid ligand. Both primers 138 and 139 are also conjugated to biotin (B). Following quantitation, a primer 1310 (named 5P7) comprising the 5' fixed sequence region of the ligand is added (not conjugated to biotin), and PCR is carried out in the presence of 5-BrdT. The PCR reaction using this primer 1310 produces the nucleic acid ligand 1311; the biotinylated products 1312 and 1313 from the quantitative PCR can be partitioned from the nascent nucleic acid ligands 1311 using streptavidin-conjugated paramagnetic beads 1314 and denaturing conditions.

In a still further embodiment nucleic acid ligands released from target beads by protease digestion are first captured by primer-conjugated paramagnetic beads and then eluted from the beads by NaOH, as described above. The eluted nucleic acid ligand is then amplified by PCR using a primer pair in which the primer that becomes incorporated into the antisense strand is conjugated to biotin. This PCR process is carried out in the presence of a fluorescent dye, such as SYBR Green described above, that binds preferentially to dsDNA, and in doing so undergoes an increase in fluorescence intensity. The change in fluorescence intensity can be used to monitor the progression of the PCR reaction and quantitate the amplification products, as described above. Following the PCR process, the dsDNA amplification products are denatured and streptavidin-conjugated paramagnetic beads are used to capture the biotinylated antisense strands. The beads are then washed and partitioned from the sense strands. A new sense strand is then made using the bead-bound antisense strand as a template in the presense of the appropriate primer, DNA polymerase, and 5-BrdU or 5-BrdT. The resulting sense strand is released from the bead and serves as the new candidate mixture for the next round of the automated SELEX process.

In the preceding embodiments, the photoSELEX process target is immobilized on a solid support, such as a paramagnetic bead, before the photocrosslinking step takes place. In preferred embodiments of the instant invention, the photoSELEX process target is immobilized after the photocrosslinking step. Such methods are provided in Attorney Docket No. SML.02, entitled "The PhotoSELEX Process: Photocrosslinking of Target in Solution," incorporated herein by reference in its entirety. According to these methods, at the beginning of each round of the automated photoSELEX process, target and candidate nucleic acid ligands are first mixed in solution and irradiated with an appropriate light dose in order to induce the formation of crosslinks between the target and the modified nucleotides of nucleic acid ligands that bind specifically to the target. The mixture is then exposed to a solid support that has been conjugated to a reagent that reacts with the target. For protein targets, suitable functionalized solid supports include, but are not limited to, tosyl-activated paramagnetic beads (such as M-280 tosyl beads, available from Dynal Corp). The tosyl groups on such beads react covalently with primary amine groups on proteins, but do not react with nucleic acid. If a target is photocrosslinked to a photoaptamer, then that photoaptamer will also be immobilized on the solid support by virtue of its covalent linkage to the target. By contrast, nucleic acids in the candidate mixture that have not photocrosslinked to target will not be covalently immobilized on the solid support. The solid support can then be partitioned from the remainder of the candidate mixture and washed under stringent, denaturing conditions (with heat and/or salt and/or detergents) to remove any nucleic acids in the candidate mixture that non-specifically and non-covalently associate with the solid support. For protein targets, immobilization onto the solid support can be performed under conditions that maximize the capture yield without regard to denaturing protein because the photocrosslinking of photoaptamer to protein has already taken place. Following capture of the target (and its photocrosslinked nucleic acid ligand), the solid support can be processed in the same manner as in the preceding embodiments, e.g., washed under stringent conditions, then treated with a reagent (such as a protease if the target is a protein) that liberates the photocrosslinked nucleic acid ligand.

Note that in all of the preceding embodiments, parasite formation during amplification of candidate nucleic acids can be reduced according to the methods provided above, e.g., by using "tailed" candidate nucleic acids and/or "tailed" primers, and/or by depleting candidate nucleic acid mixtures of those nucleic acids in which the 3' fixed sequence region fortuitously complements sequence found in the randomized sequence region, and/or by terminating PCR reactions after all primer has been incorporated.

The photocrosslinking that underpins the photoSELEX process results in the covalent modification of the desirable sequences within the mixture of candidate nucleic acid ligands. In addition, irradiation may induce photodamage to sequences within the photoSELEX candidate nucleic acid ligand mixture. Either of these modifications could conceivably lead to less than optimal replication of the desirable sequences. Therefore, in preferred embodiments, it is desirable to select those DNA polymerases and reverse transcriptases that can most efficiently replicate the modified nucleic acid. In some embodiments, the Klenow exo- fragment of *E. coli* DNA polymerase, or reverse transcriptases are used to optimize the amplification yield. In other embodiments, a combination of Taq polymerase and Pwo polymerase is used.

It is possible to push the automated photoSELEX process in the final rounds to an extreme state of enrichment that will facilitate nucleic acid ligand identification. By applying suitably stringent conditions, i.e., maximizing competition among the putative nucleic acid ligands for binding and crosslinking, the enriched pools may be driven to a state of very low sequence complexity. In the most favorable case, the final pools will be dominated by a single nucleic acid sequence that constitutes over 30% of the sequences. The identity of this "winning" nucleic acid ligand can then be easily obtained by sequencing the entire pool, avoiding the need to clone individuals from the pool prior to sequencing. Since the same selection pressures used to evolve the nucleic acid ligands in the first place are used in this final stage, albeit more extreme, the resulting winner should have both good affinity for the cognate target as well as reasonably good efficiency at crosslinking. If necessary, the SELEX process could split into a separate affinity and crosslinking set where these individual pressures could be applied to reduce pool complexity. The two resulting nucleic acid ligands could then be tested for functionality in the assay format—immobilized nucleic acid ligands that capture cognate proteins from solution followed by irreversible crosslinking. It will be appreciated that this method of using suitably stringent conditions to drive a candidate mixture to a state of low sequence complexity can also be used in the conventional SELEX process (both automated and manual) that produces non-crosslinkable nucleic acid ligands.

Example of Apparatus Design

FIGS. 7–10 show various views of an embodiment of an apparatus for performing automated SELEX according to the present invention. This embodiment is based on the Tecan™ (Cavro) robot system. It should be noted, however, that other robotic manipulation systems may also be used in the present invention, such as the MultiPROBE™ system (Packard), the Biomek 200™ (Beckman Instruments). Each view shows the apparatus during the PCR amplification stage of the automated SELEX process.

Figure 7:
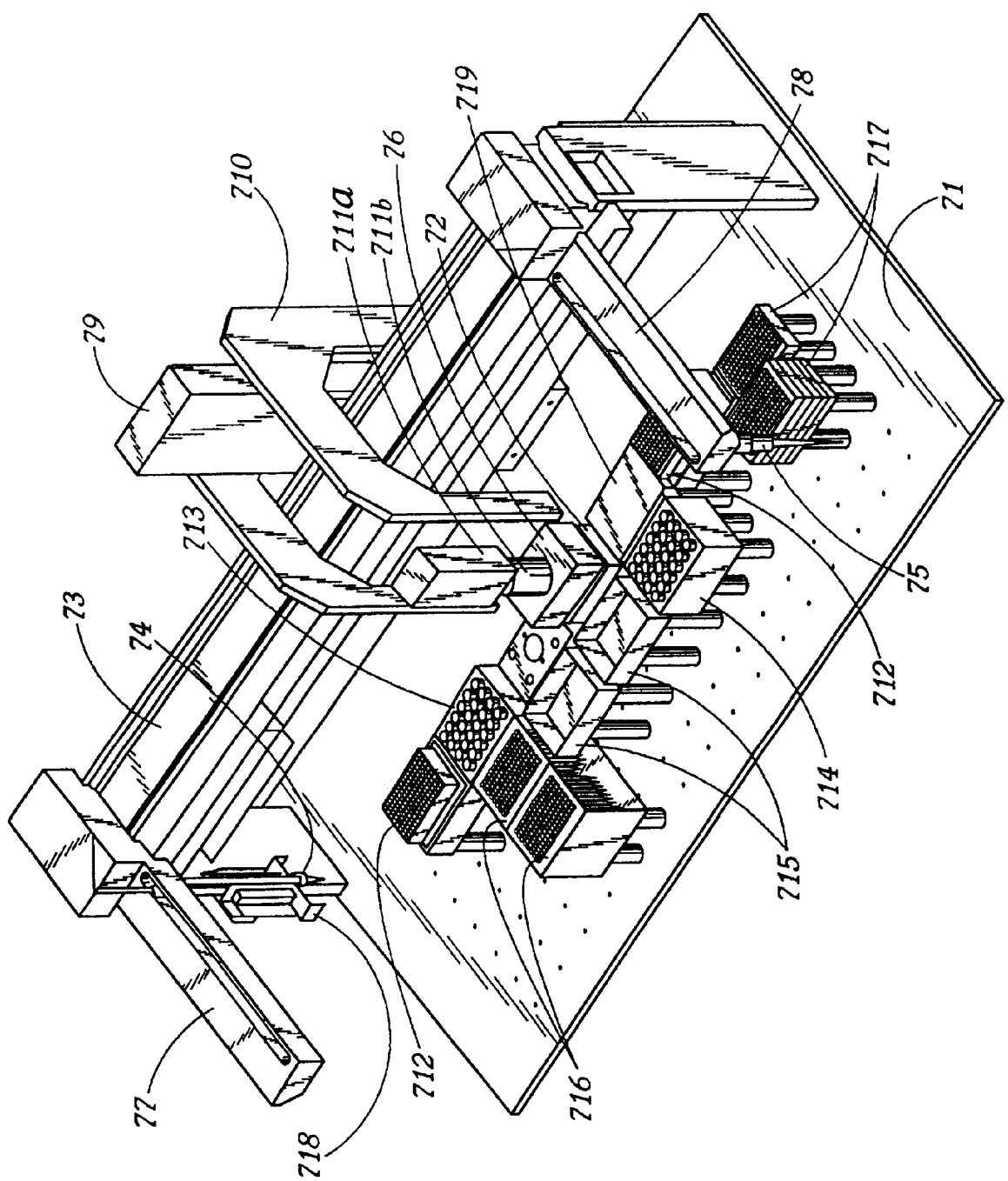
FIG. 7 shows a perspective view of an embodiment of an apparatus for performing automated SELEX according to the present invention.

In FIG. 7, a perspective view of this apparatus is shown. The system illustrated comprises a work surface 71 upon which the work station 72 is located (work station is partially obscured in this perspective view but can be seen in FIGS. 8, 9 and 10 as feature 72). The pipetting tool 74 and the aspirator 75 are attached to a central guide rail 73 by separate guide rails 77 and 78 respectively. The pipetting tool 74 can thus move along the long axis of guide rail 77; guide rail 77 can then move orthogonally to this axis along the long axis of central guide rail 73. In this way, the pipetting tool 74 can move throughout the horizontal plane; the pipetting tool can also be raised away from and lowered towards the work surface 71. Similarly, aspirator 75 is attached to guide rail 78, and guide rail 78 is attached to central guide rail 73 in such a way that aspirator 75 can move in the horizontal plane; aspirator 75 can also move in the vertical plane.

The fluorometry cover 76 is attached to guide rail 79 via bracket 710. Bracket 710 can move along the vertical axis of guide rail 79, thereby raising fluorometry cover 76 above the work station 72. When fluorometry cover 76 is positioned at the top of guide rail 79, then guide rails 77 and 78 can move underneath it to allow the pipetting tool 74 and the aspirator 75 to have access to work station 72. In this illustration, the fluorometry cover 76 is shown lowered into its working position on top of the work station 72.

Fluorometry cover 76 is attached to a CCD camera 711a and associated optics 711b. A source of fluorescent excitation light is associated with the cover 76 also (not shown). When positioned on top of the work station 72, the cover 76 allows the CCD camera 711a to measure fluorescence emission from the samples contained on the work station 72 during PCR amplification. For clarity, the light shield— which prevents ambient light from entering the fluorometry cover—is omitted from the drawing. When PCR amplification is finished, fluorometry cover 76, with attached CCD camera 711a and optics 711b, is simply raised up guide rail 79.

Figure 9:
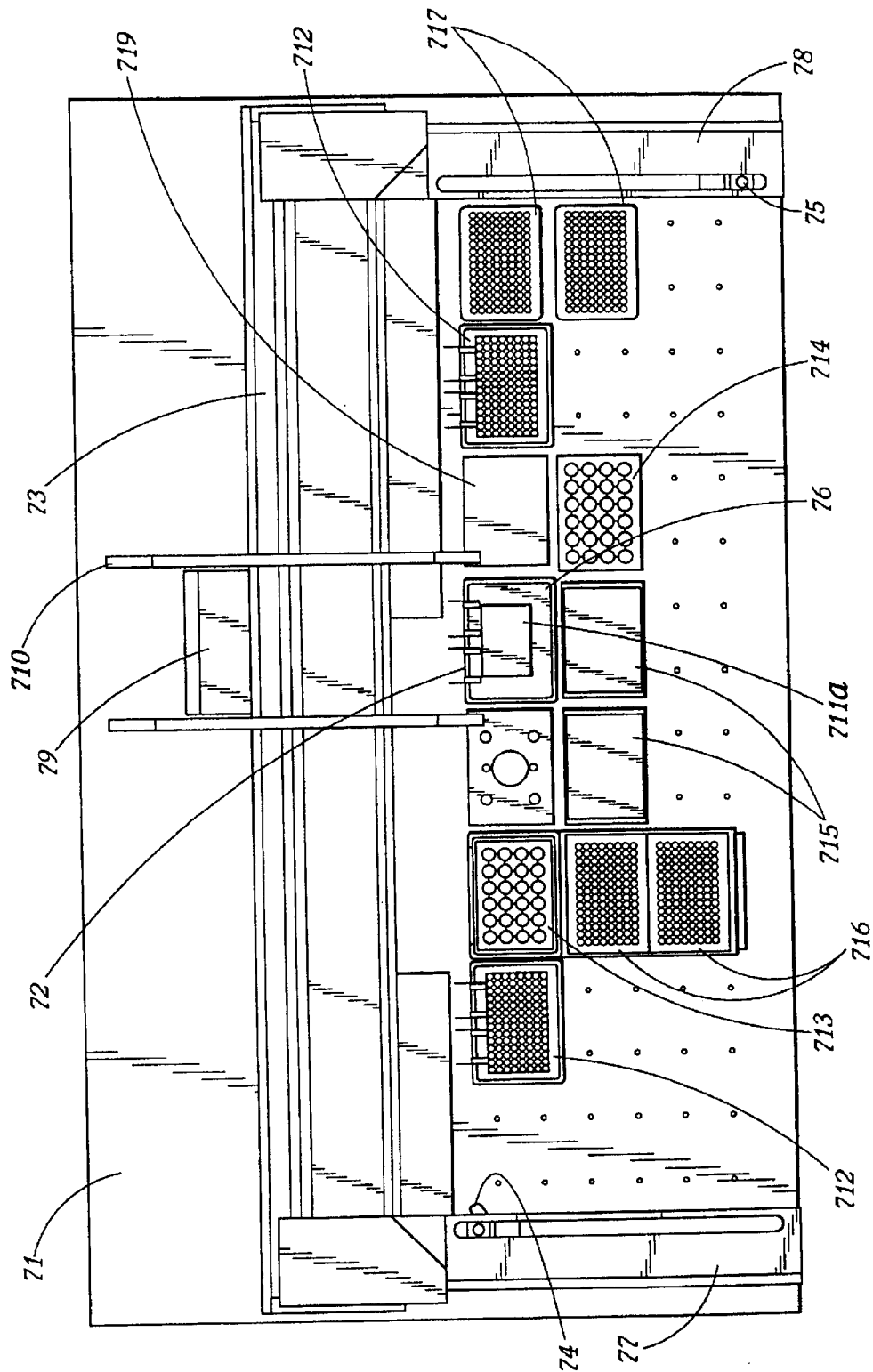
FIG. 9 shows a plan elevation view of an embodiment of an apparatus for performing automated SELEX according to the present invention.
Figure 10:
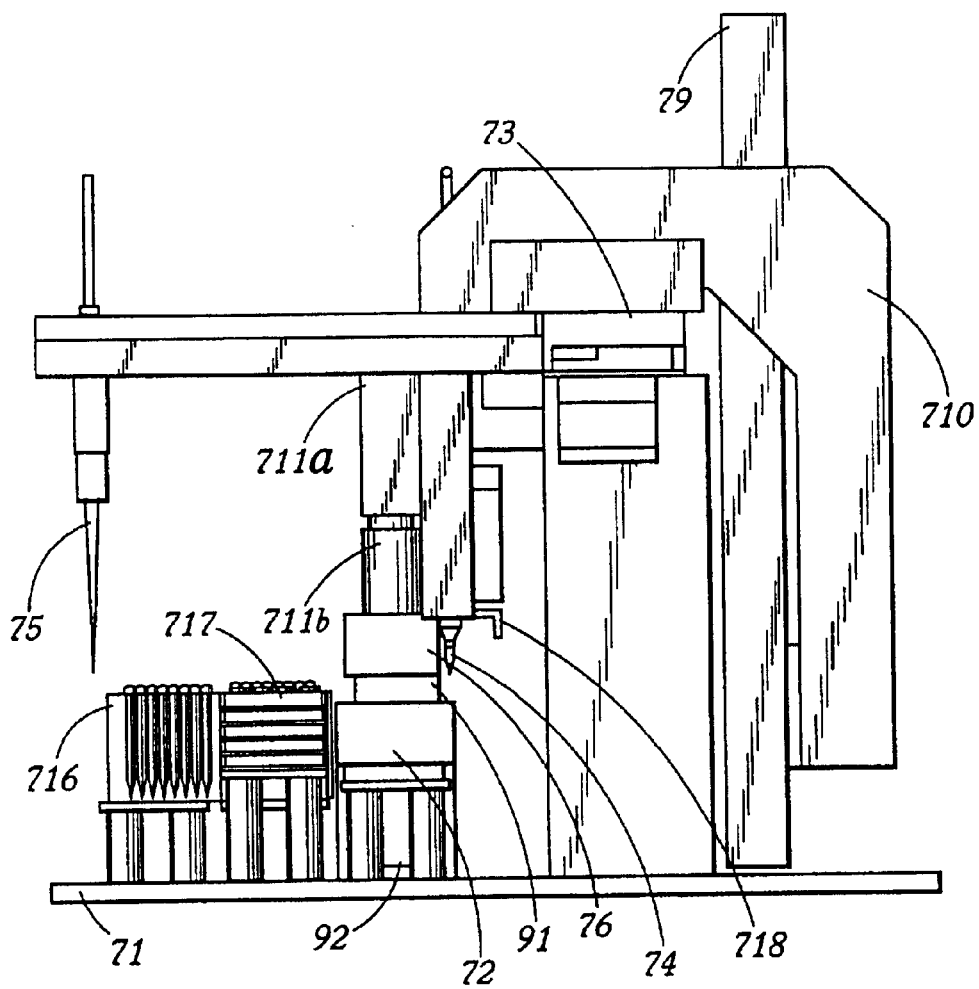
FIG. 10 shows a right side elevation view of an embodiment of an apparatus for performing automated SELEX according to the present invention.

Also not visible in this view, but visible in FIGS. 9 and 10, is the heated lid 91, which is resting on top of the work station 72 underneath the fluorometry cover 76. The work surface 71 also comprises a number of other stations, including: 4° C. reagent storage stations 712, a −20° C. enzyme storage station 713, ambient temperature reagent storage station 714, solution discard stations 715, pipette tip storage stations 716 and archive storage stations 717. Pipetting tool 74 is also associated with a gripper tool 718 that can move objects around the work surface 71 to these various storage locations. Lid park 719 (shown unoccupied here) is for storage of the heated lid (see FIGS. 9 and 10).

Figure 8:
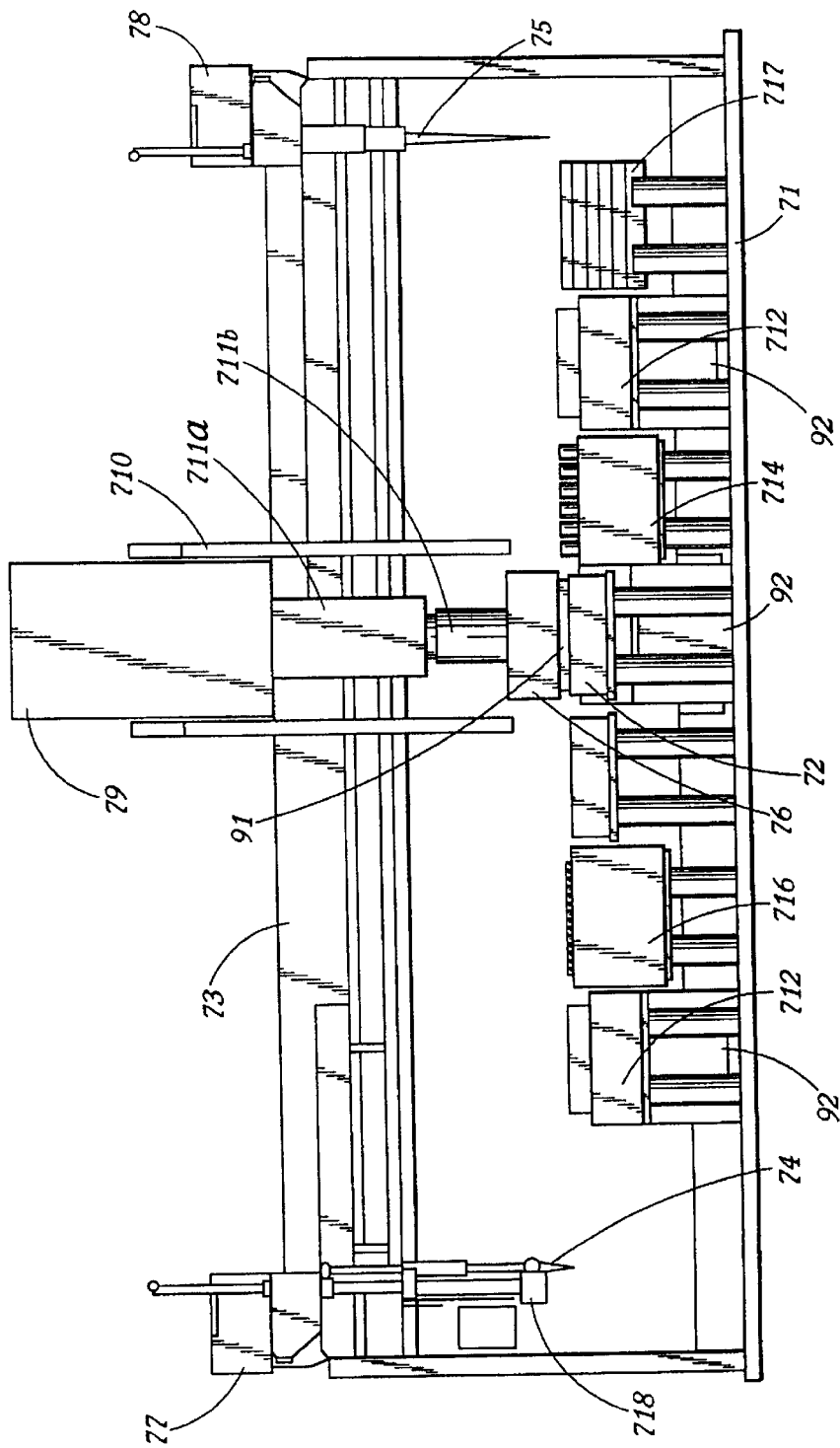
FIG. 8 shows a front elevation view of an embodiment of an apparatus for performing automated SELEX according to the present invention.

FIG. 8 shows the instrument of FIG. 7 in a plan elevation view. Each element of the instrument is labelled with the same nomenclature as in FIG. 7.

FIG. 9 is a front elevation view of the instrument in FIG. 7. Note that each element of the instrument is labelled with the same nomenclature as in FIG. 7 and FIG. 8. Note also that in this view, it can be seen that work station 72, and chilled enzyme and reagent storage stations 712 are each associated with shaking motors 92. Operation of these motors keeps the various reagents mixed during the automated SELEX process. The motors 92 are each under computer control, and can be momentarily stopped to allow reagent addition or removal, as appropriate, to the receptacle that is being agitated. Also visible in this view is heated lid 91 which is resting on top of work station 72 to insure uniform heating of the samples.

FIG. 10 is a right side elevation view of the instrument shown in FIGS. 7, 8 and 9. Every element of the instrument is labelled with the same nomenclature as in FIGS. 7, 8, and 9.

FIG. 16 illustrates another embodiment of the instrument work surface in plan view.

The operation and monitoring of the robot is controlled by computer. In preferred embodiments, the software that drives the robot is written in an object-oriented fashion, whereby each mechanical or electronic device on the robot is represented by a corresponding object in the software. Wells for holding liquid, 96-well plates, lids, tips, manipulators, or any other physical or conceptual object on the robot may also be represented by corresponding objects in the software. In particularly preferred embodiments, the software that drives the robot is written in Java. Particular devices on the robot may be driven by software written in C++ or C, for which existing libraries of method calls are already available. These software libraries are interfaced with the central software driving the robot. In preferred embodiments, software "scripts" may be written to run any desired protocol, or sequence of moves on the robot. These scripts may be written and compiled in separate files from the software which runs the robot. In particularly preferred embodiments, these scripts may be run in simulation mode, in which scripts may be tested for errors without actually running the robot.

EXAMPLES

The examples below are illustrative embodiments of the invention. They are not to be taken as limiting the scope of the invention.

Example 1

The basis of the robotic workstation is a Packard MULTIProbe 204DT™, a four probe pipetting station that utilizes disposable pipette tips to minimize nucleic acid contamination. The workspace contains a 37° C. constant temperature heat block used for equilibration of the binding reaction and in vitro transcription, a computer controlled thermal cycler for both RT and PCR reactions, a freezer unit for cold enzyme storage, various vessels for reagent storage, e.g., buffers, primers and mineral oil, and disposable pipette tip racks. The tip racks utilize the greatest area on the work surface and vary depending on the number of samples processed in parallel. All steps for in vitro selection take place either on the heat block or in the thermal cycler, liquids are transferred primarily between these two stations, although some enzyme buffers are premixed in an adjacent reagent block prior to transfer to the plate or thermal cycler.

In preferred embodiments, the entire process is controlled by software that drives the robot is written in an object-oriented fashion, whereby each mechanical or electronic device on the robot is represented by a corresponding object in the software. Ninety-six well plates, wells for holding liquid, lids, tips, manipulators, or any other physical or conceptual object on the robot may also be represented by corresponding objects in the software. In particularly preferred embodiments, the software that drives the robot is written in Java. Particular devices on the robot may be driven by software written in C++ or C, for which existing libraries of method calls are already available. These software libraries are interfaced with the central software driving the robot. In preferred embodiments, software "scripts" may be written to run any desired protocol, or sequence of moves on the robot. These scripts may be written and compiled in separate files from the software which runs the robot. In particularly preferred embodiments, these scripts may be run in simulation mode, in which scripts may be tested for errors without actually running the robot. Two way communication with the thermal cycler, established with an RS-232 connection, allows the main computer that runs the software to perform lid opening/closing operations, initiate programs stored on thermal cycler and monitor thermal cycler programs for completion. The overall software design enables complete computer control of the process, from binding reaction incubation through transcription, to occur with no user intervention.

The process begins by placing a microtiter plate coated with protein on the 37° C. block. All subsequent liquid handling up to gel purification of the enriched RNA pool is controlled by the software. During the initial two hour incubation of RNA with immobilized protein target, $dH_2O$ is periodically added to the samples (to control evaporative loss) and each solution is mixed by repeated aspiration and dispensing, so-called sip-and-spit. After the binding reaction has equilibrated, partitioning bound from free RNA is easily accomplished in this format by simply removing the RNA solution from each well; bound nucleic acid remains on the immobilized target and unbound molecules are disposed. Partitioning is followed by a series of wash steps, each wash comprised of pipetting a wash buffer solution into each well with subsequent repeated sip-and-spit mixing and finally disposal of the wash solution. The elution process begins by addition of EDTA followed by a 30 minute incubation with periodic sip-and-spit mixing. After incubation, the solution is transferred to the thermal cycler and the wells washed as described above, with the exception that each wash solution here is added to the eluted material in the cycler. The sample is then ready for enzymatic amplification.

The first step for each of the three enzyme reactions requires the preparation of a fresh enzyme solution. This is done by pipetting an aliquot of enzyme from the freezer to the appropriate buffer located in the reagent block. The viscous enzyme solution is mixed carefully and thoroughly using slow sip-and-spit mixing to avoid foaming of detergents in the enzyme solution. An aliquot of the freshly prepared RT reaction mixture is added to the dry wells of the eluted plate for a wash to remove possible eluted RNA remaining in the well. The RT reaction mixture wash is then added to the appropriate well in the thermal cycler and capped with silicone oil to prevent evaporative loss during reaction incubation at 48° C. The thermal cycler lid is closed and a program initiated for the RT reaction. The main computer monitors the reaction progress and upon detecting program completion, the lid is opened, a Taq polymerase reaction mixture is prepared and added to each completed RT reaction. This is followed by lid closure, PCR program initiation, monitoring and lid opening upon completion of PCR. An aliquot of the amplified DNA is moved from the thermal cycler to appropriate wells in the 37° C. plate for in vitro transcription of the DNA template. A freshly prepared T7 RNA polymerase solution is added to each well thoroughly mixed. A layer of silicone oil caps the reaction mixture that then incubates for 4 hours. This completes the automated process; the resulting transcribed RNA is gel purified off line and added to a microtiter plate with freshly coated protein wells for the next round of SELEX.

Typical Automated SELEX Process Run

A typical automated SELEX process run using a multi-well plate begins with loading the various reagents and materials needed to the appropriate locations on the work surface. The following steps then take place (each step performed by robot):

1) Pipette candidate nucleic acid mixture to each well of a 96 well plate on work station with one tip; tip disposed.
2) Pipette target paramagnetic beads to each well of the 96 well plate on work station; tip disposed.
3) Binding
Plate incubated at 37° C. with shaking for 30–120 minutes to allow nucleic acid ligands to interact with target on bead.
4) Bead Separation and Washing
Separate beads by placing magnetic separator cover on plate; aspirate liquid from wells; remove magnetic separator cover; dispense washing buffer to each well; incubate at 37° C. for 5 minutes with shaking.
5) Repeat step 4) for the desired number of wash cycles.
6) Elution 1
Separate beads by placing magnetic separator cover on plate and aspirate liquid from wells; remove magnetic separator cover and resuspend beads in each well in 90 $\mu$L of dH$_2$O; heat plate to 90° C. with shaking to elute nucleic acid ligands.
7) Cool plate to 48° C.
8) Prepare PCR reaction mixture in preparation vial on work surface using buffers and reverse transcriptase.
9) Pipette aliquot of PCR reaction mixture to each well on work station.
10) Reverse Transcription
Incubate plate on work station at 48° C. for 30 minutes with shaking to allow reverse transcription to take place.
11) Bead Removal 1
Place bead removal cover on plate to capture beads on magnets; move removal cover and attached beads to drop station; drop beads at drop station and wash cover at wash station.
12) Place fluorometry cover over plate on work station; place light shield over work station.
13) Amplification
Thermally cycle plate until fluorometry cover indicates that DNA saturation has occurred; calculate the amount of amplification product in each well using fluorometer readings.
14) Remove light shield and fluorometry cover; remove aliquot from each well and dispense in an archive array for storage.
15) Prepare transcription mixture in preparation vial on work surface using buffers and RNA polymerase.
16) Pipette aliquot of transcription mixture to each well on work surface.
17) Transcription
Incubate plate on work surface at 37° C. for 4 hours with shaking to allow transcription to take place.
18) Purification
Determine the volume of primer paramagnetic beads needed to retain the desired amount of RNA from each well; dispense the calculated quantity of beads to each well on work surface.
19) Incubate plate on work surface at 48° C. for 5 minutes with shaking.
20) Bead Separation and Washing
Separate primer beads by placing magnetic separation cover on plate; aspirate each well; remove separation cover; pipette wash buffer to each well; incubate plate at 48° C. for 5 minutes with shaking.
21) Repeat step 20) for the desired number of wash cycles.
22) Elution 2
Separate beads by placing magnetic separation cover on plate; aspirate each well; remove separation cover; pipette 100 $\mu$L dH$_2$O to each well; incubate plate on work station at 95° C. for 3 minutes with shaking to elute RNA from primer beads.
23) Bead Removal 2
Place bead removal cover on plate to capture beads on magnets; move removal cover and attached beads to drop station; drop beads at drop station and wash cover at wash station.
24) Begin at step 2) again for the desired number of cycles.

Example 2

The following example describes the performance of automated SELEX on the recombinant murine P-selectin/IgG fusion protein (PS-Rg). For a description of manual SELEX against selectin targets see Parma et al, U.S. Pat. No. 5,780,228, entitled, "High Affinity Nucleic Acid Ligands to Lectins," incorporated herein by reference in its entirety.

Passive adsorption of IgG proteins to polystyrene surfaces through hydrophobic interactions has been successfully used in a variety of immunoassays. Enough IgG remains active under such immobilization to be useful as a capture reagent in ELISA tests. Some fraction of the adsorbed molecules maintain their active conformation in the antigen binding site, replaced here with P-selectin. Thus, it was determined that PS-Rg immobilized on Immulon 1 polystyrene plates could serve as a target for the automated SELEX process.

A. Plate Characterization

1. Test of Various Blocking Agents

Figure 1:
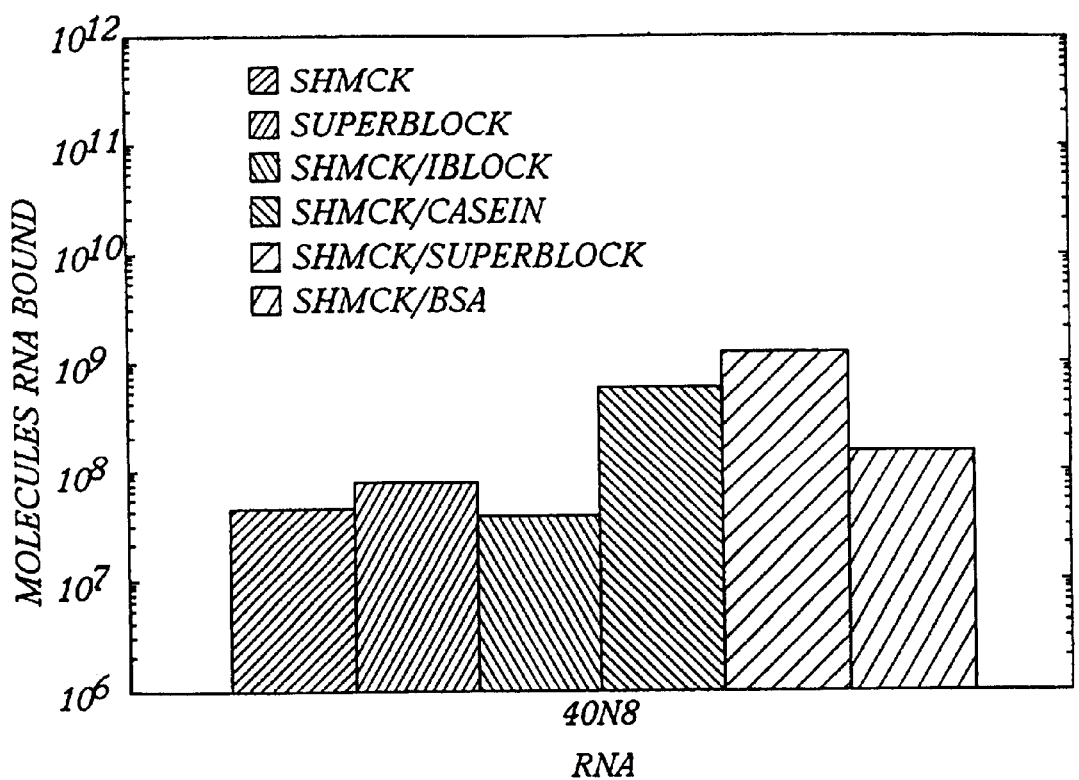

To empty Immulon 1 wells, 150 $\mu$l of various buffers were incubated for 30 minutes at room temperature including the following:

(1) SHMCK (10 mM HEPES pH 7.3, 120 mM NaCl, 5 mM KCl, 1 mM MgCl$_2$, 1 mM CaCl$_2$)
(2) SuperBlock (Pierce)
(3) SHMCK+0.1% I-Block (Tropix)
(4) SHMCK+0.1% Casein (Sigma)
(5) SHMCK+SuperBlock (1:1)
(6) SHMCK+1% BSA The wells were then washed six times with 150 $\mu$l of SIT (SHMCK, 0.1% I-Block, 0.05% Tween 20) buffer. Then 200 pmoles of 40N8 candidate mixture RNA in SIT buffer were added to each well and incubated for 2 hours at 37° C. The wells were washed six times with 150 $\mu$l SIT buffer. To each well 75 $\mu$l of dH$_2$O was added and heated to 95° C. for 5 minutes to elute the RNA from the plate. To this 25 $\mu$l of an RT mix was added and incubated as described. The eluant was then measured offline for amount of RNA present by qPCR. The results of this experiment are shown in FIG. 1.

2. Role of Buffer Components in Background on Unblocked Immulon 1 Plates

To empty Immulon 1 wells, 200 pmoles of 40N8 was added in 100 $\mu$l of the following buffers and incubated at 37° C. for 2 hours:

(1) SIT (SHMCK, 0.1% I-Block, 0.05% Tween 20)
(2) SHMCK
(3) SA (SHMCK, 0.01% HSA)

(4) ST (SHMCK, 0.05% Tween 20)
(5) SAT (SHMCK, 0.01% HSA, 0.05% Tween 20)

Figure 2:
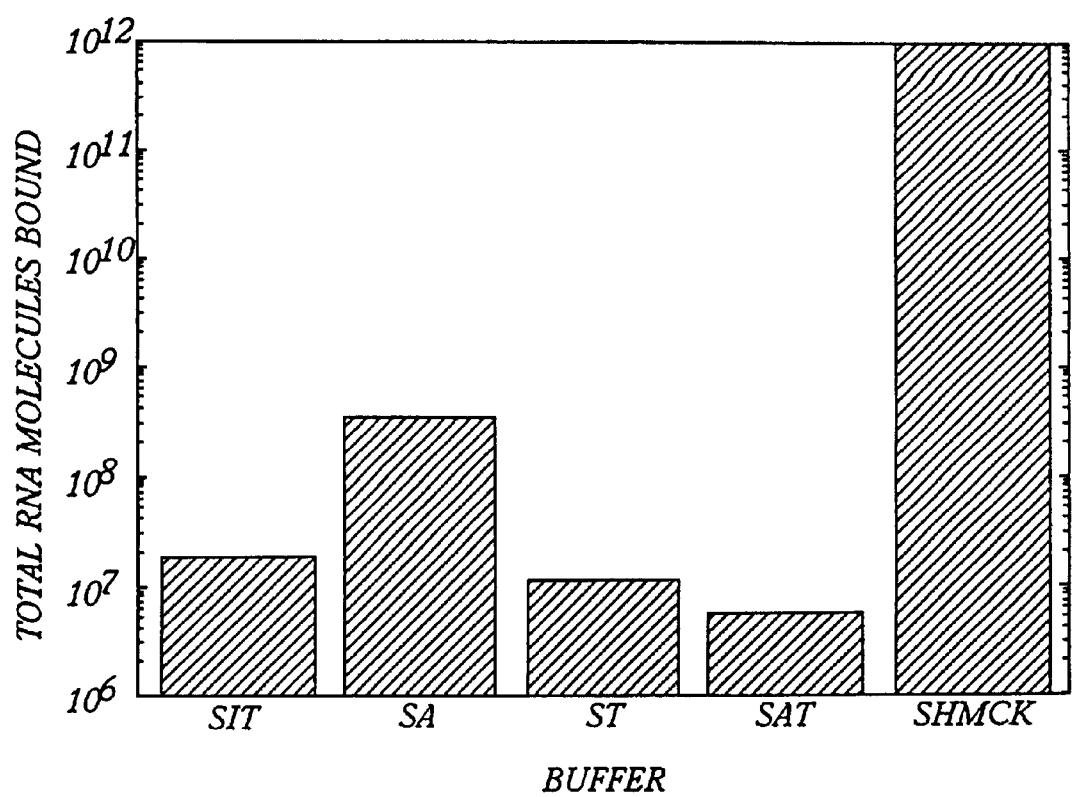

The wells were subsequently washed six times with 150 µl of the appropriate buffer and eluted with SHKE as described. The eluant was then measured for the amount of RNA present by RT as described followed by qPCR. The results of this experiment are shown in FIG. 2.

Figure 3:
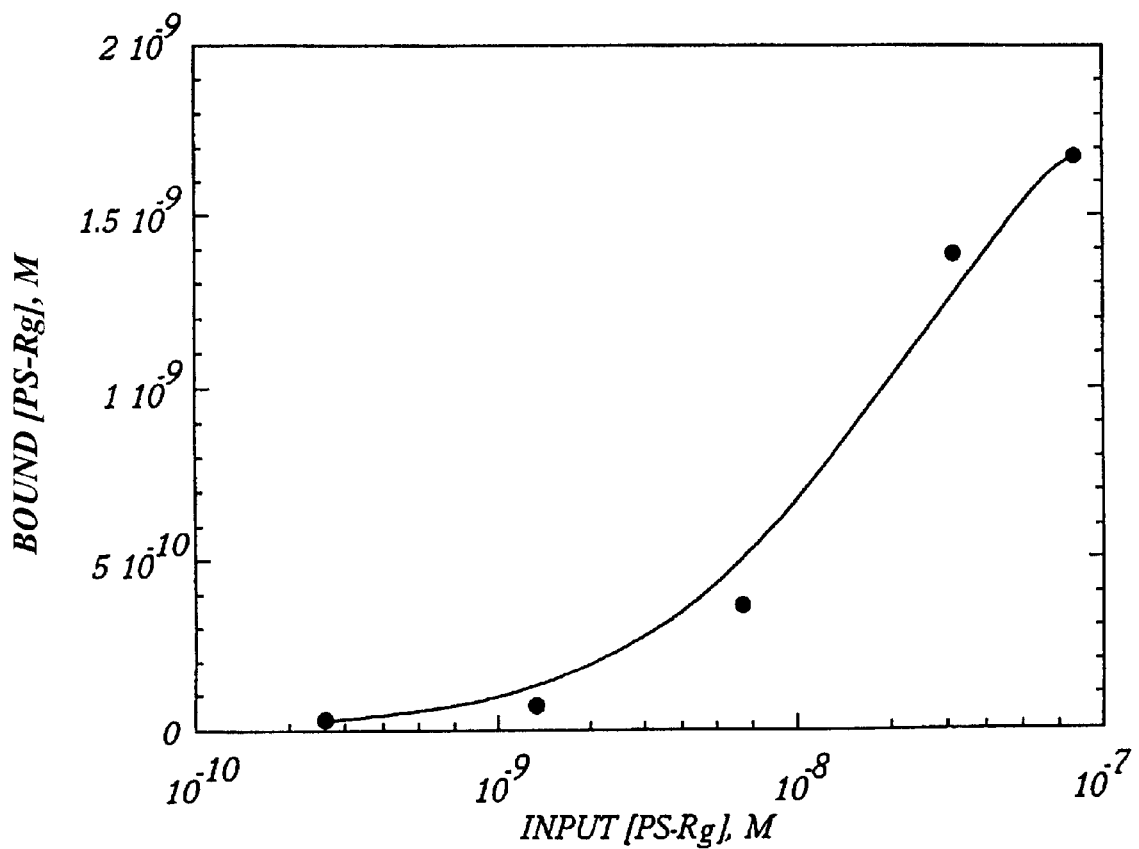

B. Measurement of the Amount of PS-Rg Capable of Binding to Aptamer 1901 After Protein Immobilization Murine PS-Rg, a recombinant murine selectin/IgG fusion, was purchased from D. Vestweber. Hydrophobic binding of PS-Rg to the plate surface was measured by loading fixed amounts of PS-Rg, washing as described above, and then performing a binding curve by titrating a high affinity RNA aptamer 1901 ($K_d$=22 pM) that binds to the native conformation of the active site of PS-Rg. This was done with several protein concentrations. FIG. 3 shows a plot of the amount of PS-Rg capable of binding aptamer 1901 (i.e., active PS-Rg) as a function of the input protein concentration. The plateau values of these binding curves then are taken as a representation of the amount of active protein bound to the surface, assuming a 1:1 stoichiometry. Using these data, it was determined that the plate was near saturated (calculated saturation is 220 fmol/well PS-Rg) when loading 4 µg/ml PS-Rg, representing 150 fmoles of bound PS-Rg.

C. EDTA Elution Study with Murine PS-Rg

Figure 4:
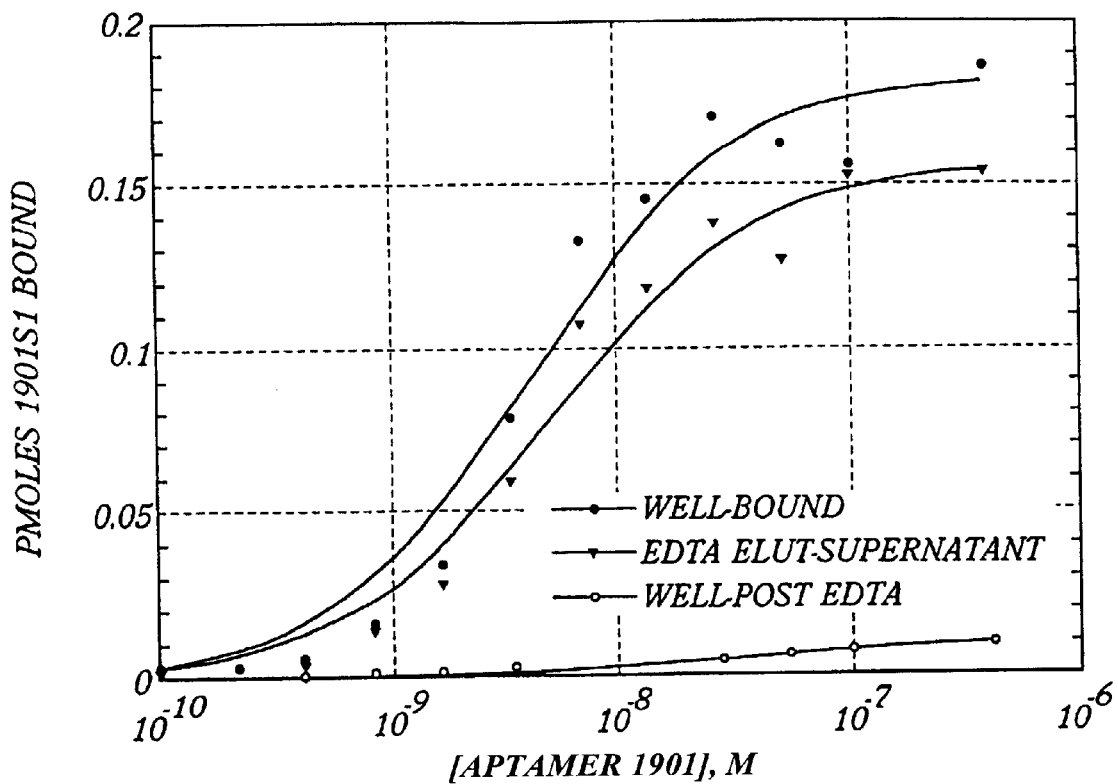

EDTA can be used to elute aptamers that have bound to the native conformation of the active site of PS-Rg. Without being bound to any one theory, it is believed that this elution results from the disruption of the native structure of the $Ca^{2+}$-dependent active site of P-selectin. Murine PS-Rg at 4 µg/ml was coated onto empty wells in 75 µl SHMCK for 2 hours at room temperature and washed as described. Then a titration of 3 fmoles to 20 pmoles of $^{32}$P-labeled RNA aptamer clone 1901 ($K_d$=22 pM), isolated from a previous manual SELEX experiment, was coated on two sets of control and PS-Rg wells for 2 hours at 37° C. and washed as described. One set of control and PS-Rg wells were then removed and monitored for $^{32}$P-RNA bound by scintillation counting. Fifty µl of SHKE (10 mM HEPES pH 7.3, 120 mM NaCl, 5 mM KCl, 5 mM EDTA) was then added to the other set of dry wells and incubated with mixing at 37° C. for 30 minutes. The buffer was then removed and $^{32}$P-labeled RNA was measured by scintillation counting. The results of this experiment are shown in FIG. 4 as a plot of total binding of $^{32}$P-labeled aptamer (pmoles) as a function of total aptamer concentration (M). It can be seen that saturable binding of aptamer 1901 was achieved when PS-Rg was present on the plate surface. It is also evident from FIG. 4 that EDTA elution of aptamer bound to PS-Rg on the plate surface was quite successful, with little material (<1% of total RNA bound/well) left in the well after elution with SHKE. The amount of active protein on the plate can be estimated as approximately 200 fmoles from the plateau value of aptamer binding and the assumption of a 1:1 stoichiometry for the interaction.

D. Automated SELEX Process Using Immobilized PS-Rg as Target

1. Automated Selection

Murine PS-Rg was manually coated at varying concentrations in 75 µl SHMCK buffer for two hours at room temperature (23° C.) onto a round bottom immulon 1 polystyrene 96 well microtiter plate. Control wells were prepared by coating SHMCK alone. The plate was then washed six times with 150 µl SAT and 200 pmoles of gel purified 40N8 RNA pool was added in 75 µl SAT buffer. The plate was placed on a 37° C. heat block (USA Scientific) mounted on a MultiPROBE 204DT pipetting workstation (Packard) and samples were incubated uncovered at 37° C. for two hours. All subsequent steps were performed by the robotic workstation except where noted. Every twenty minutes during the incubation of the RNA with the plate, 5 µl of $dH_2O$ was added to compensate for evaporative loss (rate of loss measured at 14.5+0.4 µl/hour) and to mix the reactions. Plates were then washed six times with 150 µl SAT buffer.

To the dried plate 75 µl of SHKE (10 mM HEPES pH 7.3, 120 mM NaCl, 5 mM KCl, 5 mM EDTA) was added to the plate in order to elute bound RNA, and incubated at 37° C. for 30 minutes with mixing every ten minutes. The supernatant containing the eluted RNA was then removed from the plate and added to an MJ Research thermocycler mounted on the work station with remote command capabilities. The eluted RNA was then amplified as described in the following section.

2. Automated Amplification

Again, all steps were performed by the robotic workstation, except where noted. AMV reverse transcriptase (Boehringer Mannheim) stored in a pre-chilled Styrofoam cooler mounted on the work surface at below 0° C., was added to a prepared RT (Reverse Transcriptase) buffer and thoroughly mixed. Twenty five µl of the resulting RT Mix (50 mM Tris-HCl pH 8.3, 60 mM NaCl, 11 mM $Mg(OAc)_2$, 10 mM DTT, 1 mM DATP, 1 mM dTTP, 1 mM dGTP, 1 mM dCTP, 400 pmoles 3P8, 20 units AMV-RT/reaction) was then added to the empty incubation wells and mixed to provide a wash for the well. The RT mix was then moved into the thermocycler, added to the eluted RNA, and thoroughly mixed. To this 25 µl of silicone oil (Aldrich) was added to prevent evaporation. The thermocycler was then remotely turned on by the computer. The lid was closed and the reaction incubated at 48° C. for 30 minutes followed by 60° C. for 5 minutes. Upon completion of the RT reaction the lid was triggered to open and 10 µl of the reaction was manually removed to be measured manually by quantitative PCR (qPCR).

Taq polymerase (Perkin Elmer) stored in the Styrofoam cooler, was added to a prepared PCR buffer (Perkin Elmer Buffer 2 (50 mM KCL, 10 mM Tris-HCl pH 8.3), 7.5 mM $MgCl_2$, 400 pmoles 5P8) and thoroughly mixed. 100 µl of the Taq mix was then added to each well, the lid closed, and PCR was initiated. PCR was run under the following conditions: 93° C. for 3 minutes followed by a loop consisting of 93° C. for 1 minute, 53° C. for 1 minute, and 72° C. for 1 minute for n cycles where n was determined by the input amount of RNA to the RT reaction (see qPCR description below and Example 3). Upon completion of PCR the lid was opened and 50 µl was removed and added to an empty plate well on the fixed 37° C. heat block.

T7 RNA polymerase (Enzyco) stored in the Styrofoam cooler, was added to a prepared Transcription buffer (40 mM Tris-HCl pH 8, 4% (w/v) PEG-8000,12 mM $MgCl_2$, 5 mM DTT, 1 mM Spermidine, 0.002% Triton X-100, 100 units/ml pyrophosphatase (Sigma)) and thoroughly mixed. 200 µl of the Transcription buffer was then added to the PCR product well and mixed. To this reaction a 25 µl layer of silicone oil was added and the reaction was incubated for 4 hours at 37° C. The completed reaction was then removed and purified manually by PAGE. A portion of the purified RNA was then used to initiate the next round of the SELEX process. Five rounds of the SELEX process were performed.

3. Results of the Automated SELEX Process

Figure 5:
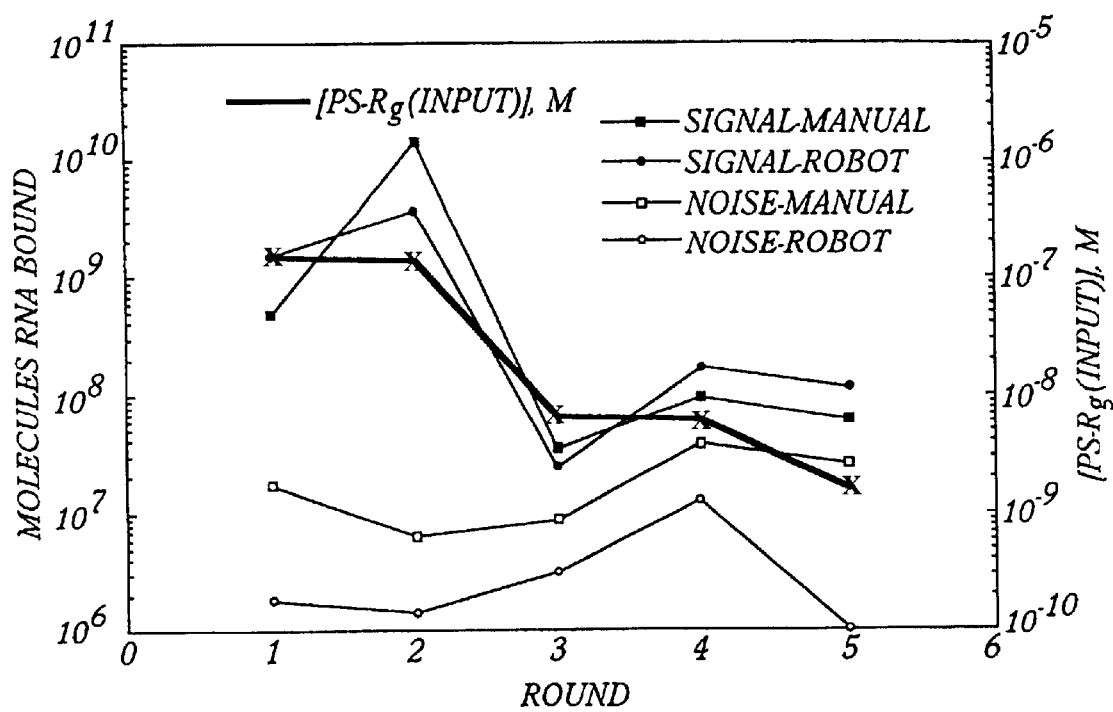

Table 1 below outlines the progress of the PS-Rg SELEX process experiment performed according to the methods described above. PS-Rg loading is indicated in μg/ml concentrations. The signal measured represents the number of RNA molecules bound to the wells containing PS-Rg as determined by qPCR for each sample. Similarly, noise is representative of the number of RNA molecules bound to control wells containing no protein. FIG. 5 illustrates this data in graphical form.

TABLE 1

Progress of the PS-RG SELEX Experiment.

| Round | PS-Rg, μg/ml Loaded | Signal Manual | Noise Manual | Signal/ Noise Manual | Signal Robot | Noise Robot | Signal/ Noise Robot |
|---|---|---|---|---|---|---|---|
| 1 | 4 | 4.8e + 8 | 1.8e + 7 | 2.7 | 1.5e + 9 | 1.8e + 6 | 833 |
| 2 | 4 | 1.6e + 10 | 6.6e + 6 | 2424 | 4.2e + 9 | 1.5e + 6 | 2800 |
| 3 | 0.2 | 4e + 7 | 1e + 7 | 4 | 2.8e + 7 | 3.4e + 6 | 8.2 |
| 4 | 0.2 | 1.1e + 8 | 4.5e + 7 | 2.5 | 2e + 8 | 1.5e + 7 | 13.3 |
| 5 | 0.2 | 3.1e + 8 | 3.1e + 7 | 10 | 1.4e + 8 | 1e + 6 | 140 |

Figure 6:
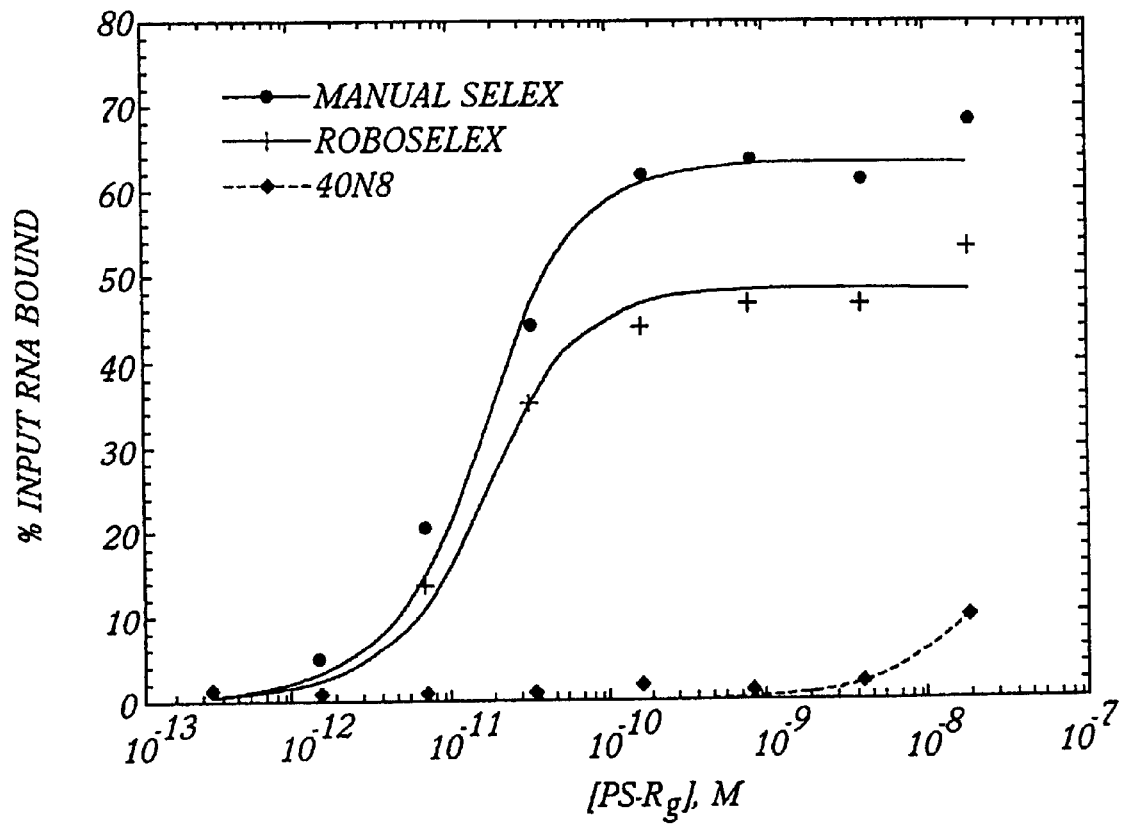
FIG. 6 depicts the solution phase binding curves of round 5 RNA pools to murine PS-Rg protein. The binding curve measured for the enriched round five RNA pool generated with the automated SELEX process (+) is compared to the manual process (filled circles) as well as the starting random RNA pool (filled diamonds).

Solution phase binding curves of the enriched round 5 RNA pool from both the automated SELEX process (+) and the manual SELEX process (filled circles), and of the initial RNA candidate mixture (filled diamonds) are illustrated in FIG. 6. The affinity of the starting candidate mixture is ~100 nm; after 4 rounds of either manual or automated SELEX, the affinity increased to 6 pM, an improvement of 4 orders of magnitude.

Example 3

Quantitative PCR

The following primers (5P7-FD2 and 5P8-FD2) were designed wherein the underlined portions are complementary to the N7 and N8 templates.

```
5P7-FD2
        DABCYL
          |
        (CH2)6
   A      |
        GCTCTAATACGACTCACTATAGGGAGGACGATGCGG-3'
   A    ||||                  5P7        SEQ ID NO:1
        CGAG-5'
   G      |
        6-FAM
5P8-FD2
        DABCYL
          |
        (CH2)6
   A      |
        GCTCTAATACGACTCACTATAGGGAGACAAGAATAAACGCTCAA-3'
   A    ||||                  5P8        SEQ ID NO:2
        CGAG-5'
   G      |
        6-FAM
```

The hairpin in each primer has a Tm of ~85° C., and contains a fluorophore (6-FAM) on its 5' terminus and a quencher (DABCYL) opposite the fluorophore on its stem. Upon illumination at 495 nm, excitation energy is transferred from 6-FAM to DABCYL by fluorescence resonance energy transfer. The efficiency of energy transfer is dependent on the sixth power of the distance between the fluorophore and quencher. Because the fluorophore and quencher are in very close proximity in the closed hairpin conformation, little signal is generated by unincorporated primer. However, as primer is incorporated into product during PCR, the fluorophore and quencher are further separated by a distance of 10 base pairs, and signal is increased. The increase in signal is directly proportional to the amount of product formed.

A standard curve using 40N8 cDNA template ($10^6$–$10^{10}$ copies/25 μL reaction), primers 5P8 and 3P8 (80 pmoles) and the fluorescent primer 5P8-FD2 (16 pmoles) in a PCR reaction was prepared as a linear plot and as a semi-log plot (not shown). Fluorescein signal (normalized to an internal reference dye and background-subtracted) was plotted as a function of PCR cycle number. In early PCR cycles, product was generated exponentially in all reactions; however, background signal exceeded product signal. The cycle at which product signal exceeded background was dependent on the starting template copy number. A signal threshold level can be chosen above the background level, and the cycle at which each reaction crosses the threshold (Ct) can then be plotted as a function of template copy number to generate a standard curve. The equation for the standard curve can then be used to calculate template copy numbers in unknowns based on the Ct values.

This quantitative PCR technique was used to measure signal to noise ratios and absolute template copy number in a SELEX targeting PDGF adsorbed to polystyrene plates. Because very low protein loadings were used (<100 amol/ reaction), quanfitation by radiation was not possible. The amplification plot (not shown) illustrated the quantitation of 10 amol RNA bound to the background well and 600 amol RNA bound to the target well, for a signal-to-noise ratio of 60.

Example 4

A candidate mixture of nucleic acids comprising the following sequences was synthesized (wherein N=A,G,C, or T):

30N7.1     5'-GGGAGGACGATGCGG[N]$_{30}$CAGACGACGAGCGGGA-3' SEQ. ID. NO:3

The SELEX process was then started using in Round 1, $1\times10^{12}$ copies of the 30N7.1 candidate mixture. The mixture was amplified by PCR during round 1 in a 100 μL reaction containing 100 pmol each of tailed primers (AT)$_4$5P7 and (T)$_8$3P7.1 having the following sequences:

SEQ. ID. NO:4
(AT)$_4$-5P7     5'-ATATATATGGGAGGACGATGCGG-3'

SEQ. ID. NO:5
(T)$_8$-3P7.1    5'-TTTTTTTTTCCCGCTCGTCGTCTG-3'

Forty PCR cycles were performed with a 2-step thermal profile (denaturation at 95° C. for 15 seconds, annealing and extension at 60° C. for 60 seconds). In Rounds 2–6 of the SELEX process, $1\times10^{12}$ copies of crude double-stranded DNA product from the previous round were amplified as in Round 1. Following PCR, 2 μL of each sample were run on an 8% polyacrylamide gel containing 7M urea, stained with SYBR Gold, and imaged on a FUJI FLA-3000. FIG. 11 depicts the resulting gel image. It can be seen that after 6 rounds of the SELEX process, product of the correct size predominates, with no discernible high molecular weight species. By contrast, if the same primers minus the 5' tail sequences are used, parasites form in Round 1 and quickly become the dominant species in the candidate mixture during Round 2.

Example 5

The following candidate nucleic acid mixtures and tailed primers were synthesized. Tm indicates the calculated melting temperature the entire tailed-primer molecule.

```
Candidate Nucleic Acid Mixtures:
40N11      5'-GGCTGATGACGTAGCGGC[N]40CCGAAAGGAACAACAGAG-3'                        SEQ. ID. NO:6

(AT)4-40N11-(A)8
5'-ATATATATGGCTGATGACGTAGCGGC[N]40CCGAAAGGAACAACAGAGAAAAAAAA-3'                  SEQ. ID. NO:7

(AT)4-40N12-(A)8
5'-ATATATATGCCGTAGTGATCGCTCGG[N]40GCGAAACGACAAGAAGACAAAAPAAA-3'                  SEQ. ID. NO:8

(AT)4-40N13-(A)8
5'-ATATATATCGTGTGAGCTGCTGGCCG[N]40CCGACAGGAAGAGCACACAAAAAAAA-3'                  SEQ. ID. NO:9

(AT)4-40N14-(A)8
5'-ATATATATGCGGATCAGCTTGCACCG[N]40GCCAGAAGCAGAAGGACGAAAAAAAA-3'                  SEQ. ID. NO:10

(AT)4-40N15-(A)8
5'-ATATATATCGTCGCAGCTGGCGCTGG[N]40GGGAACACAGACGACCGCAAAAAAAA-3'                  SEQ. ID. NO:11

(AT)4-40N16-(A)8
5'-ATATATATCGCGCAGCTGCCTGTCGC[N]40GGCAGACAGCAACACGGGAAAAAAAA-3'                  SEQ. ID. NO:12

(AT)4-40N17-(A)8
5'-ATATATATGCGTGCCGTCGCGGCCCG[N]40CGGAGCAGCAGGCACACCAAAAAAAA-3'                  SEQ. ID. NO:13

(AT)4-40N18-(A)8
5'-ATATATATGCGGGCGTCCGTGCGGTC[N]40GAGCCACGCCACAGCAGGAAAAAAAA-3'                  SEQ. ID. NO:14

5' Tailed Primers:

5P11              5'-GGCTGATGACGTAGCGGC-3'                                        SEQ. ID. NO:15

(AT)4-5P11      5'-ATATATATGGCTGATGACGTAGCGGC-3'   Tm = 66° C.                    SEQ. ID. NO:16

(AT)4-5P12      5'-ATATATATGCCGTAGTGATCGCTCGG-3'   Tm = 66° C.                    SEQ. ID. NO:17

(AT)4-5P13      5'-ATATATATCGTGTGAGCTGCTGGCCG-3'   Tm = 69° C.                    SEQ. ID. NO:18

(AT)4-5P14      5'-ATATATATGCGGATCAGCTTGCACCG-3'   Tm = 69° C.                    SEQ. ID. NO:19

(AT)4-5P15      5'-ATATATATCGTCGCAGCTGGCGCTGG-3'   Tm = 72° C.                    SEQ. ID. NO:20

(AT)4-5P16      5'-ATATATATCGCGCAGCTGCCTGTCGC-3'   Tm = 72° C.                    SEQ. ID. NO:21

(AT)4-5P17      5'-ATATATATGCGTGCCGTCGCGGCCCG-3'   Tm = 75° C.                    SEQ. ID. NO:22

(AT)4-5P18      5'-ATATATATGCGGGCGTCCGTGCGGTC-3'   Tm = 75° C.                    SEQ. ID. NO:23

3' Tailed Primers:

3P11              5'-CTCTGTTGTTCCTTTCGG-3'                                        SEQ. ID. NO:24

(T)8-3P11       5'-TTTTTTTTCTCTGTTGTTCCTTTCGG-3'   Tm = 66° C.                    SEQ. ID. NO:25

(T)8-3P12       5'-TTTTTTTTGTCTTCTTGTCGTTTCGC-3'   Tm = 66° C.                    SEQ. ID. NO:26

(T)8-3P13       5'-TTTTTTTTGTGTGCTCTTCCTGTCGG-3'   Tm = 69° C.                    SEQ. ID. NO:27

(T)8-3P14       5'-TTTTTTTTCGTCCTTCTGCTTCTGGC-3'   Tm = 69° C.                    SEQ. ID. NO:28

(T)8-3P15       5'-TTTTTTTTGCGGTCGTCTGTGTTCCC-3'   Tm = 72° C.                    SEQ. ID. NO:29

(T)8-3P16       5'-TTTTTTTTCCCGTGTTGCTGTCTGCC-3'   Tm = 72° C.                    SEQ. ID. NO:30

(T)8-3P17       5'-TTTTTTTTGGTGTGCCTGCTGCTCCG-3'   Tm = 75° C.                    SEQ. ID. NO:31

(T)8-3P18       5'-TTTTTTTTCCTGCTGTGGCGTGGCTC-3'   Tm = 75° C.                    SEQ. ID. NO:32
```

The SELEX process was then started using untailed 40N11 candidate nucleic acid mixture (with the untailed primers 5P11 and 3P11), $(AT)_4$-40N11-$(A)_8$ tailed candidate nucleic acid mixture (with the tailed primers $(AT)_4$-5P11 and $(T)_8$-3P11), $(AT)_4$-40N17-$(A)_8$ tailed candidate nucleic acid mixture (with the tailed primers $(AT)_4$-5P17 and $(T)_8$-3P17), and $(AT)_4$-40N18-$(A)_8$ tailed candidate nucleic acid mixture (with the tailed primers $(AT)_4$-5P18 and $(T)_8$-3P18). In Round 1 of the SELEX process, $1 \times 10^{12}$ copies of each candidate nucleic acid mixture served as template for PCR amplification in a 100 µL reaction containing 100 pmol each of the appropriate primers. Forty cycles were performed with a 2-step thermal profile (denaturation at 95° C. for 15 seconds, annealing and extension at 2° C. below the calculated primer Tm for 60 seconds). At this temperature, the primer anneals to the fixed region of the candidate nucleic acid mixture, but the tail will be unstable. In all subsequent rounds of the SELEX process, $1 \times 10^{12}$ copies of crude double-stranded DNA product from the previous round were amplified as in Round 1. Following PCR, 2 µL of each sample were run on an 8% polyacrylamide gel containing 7M urea, stained with SYBR Gold, and imaged on a FUJI FLA-3000. The results are illustrated in FIG. 12. The arrows in FIG. 12 indicate the size of the correct PCR product. It can be seen that while parasites appeared in Round 2 with untailed N11, no parasites appeared until Round 15 with tailed N11, or until Round 10 with tailed N17 and tailed N18.

Example 6

The effect of parasite contamination on PCR reactions was assayed with either tailed N11 primers and candidate nucleic acid mixture (primers $(AT)_4$-5P11 and $(T)_8$-3P11, and candidate nucleic acid mixture $(AT)_4$-40N11-$(A)_8$) or untailed primers and candidate nucleic acid mixture (primers 5P11 and 3P11, and candidate nucleic acid mixture 40N11). $1 \times 10^{12}$, $1 \times 10^{10}$, $1 \times 10^{8}$, $1 \times 10^{6}$ or 0 copies of candidate nucleic acid mixture served as template for PCR amplification in a 100 µL reaction containing 100 pmol each primer, and 1 µL of N11 parasite (~$1 \times 10^{12}$ copies of product from Round 6 of the N11 parasite assay from Example 5 and FIG. 12 ). Forty cycles were performed with a 2-step thermal profile (denaturation at 95° C. for 15 seconds, annealing and extension at 64° C. for 60 seconds). Following PCR, 2 µL of each sample were run on an 8% polyacrylamide gel containing 7M urea, stained with SYBR Gold, and imaged on a FUJI FLA-3000. The resulting gel is depicted in FIG. 13. The arrows in FIG. 13 indicate the size of the correct PCR product. The result indicates that with untailed N11 primers, parasites dominated even with $1 \times 10^{12}$ copies of N11 candidate nucleic acid mixture present. With tailed N11 primers, full-length product dominated even with as little as $1 \times 10^{6}$ copies of candidate nucleic acid mixture; no parasites were evident in reactions where the candidate nucleic acid mixture copy number was greater than $1 \times 10^{8}$. Product appearing in the 0 candidate nucleic acid mixture copy number samples results from amplification of template molecules contaminating one of the common reaction components.

Example 7

Scheme for the Synthesis of Benzophenone-labeled Dynal M-270 Beads

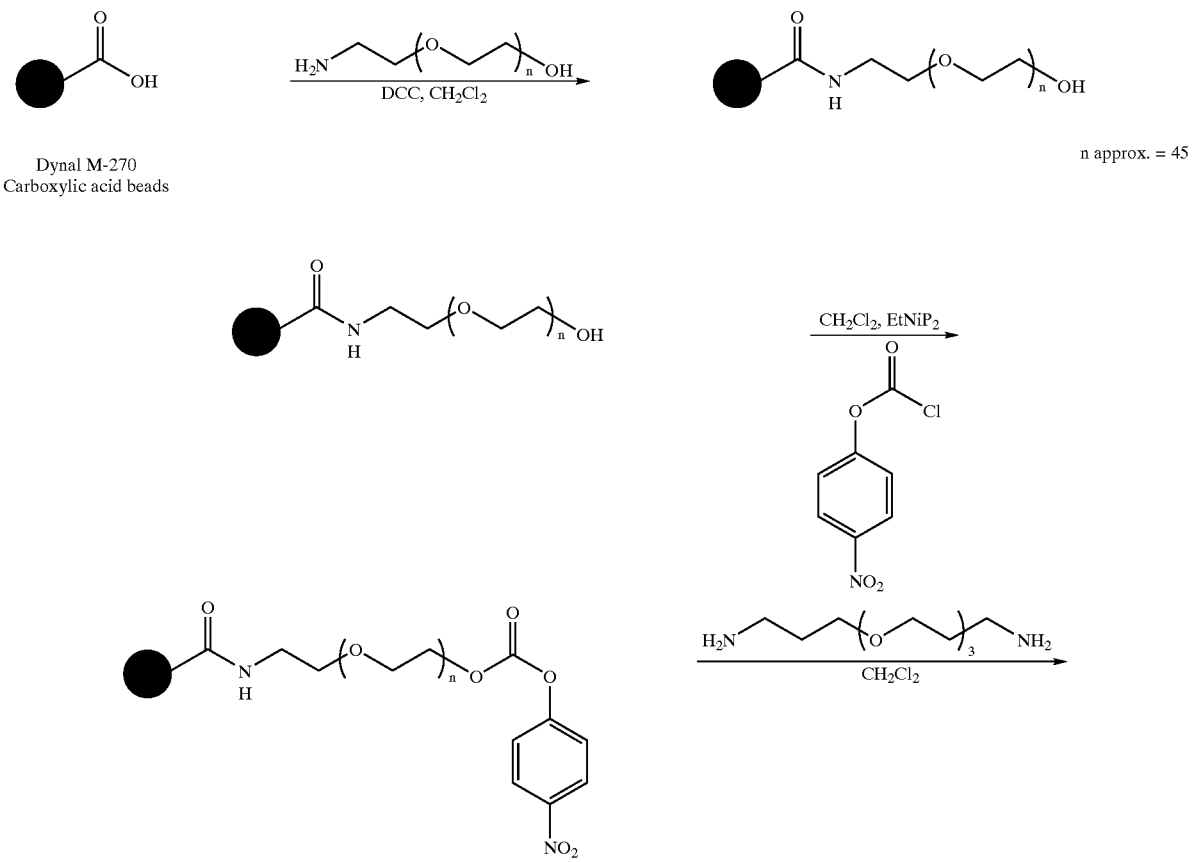

-continued
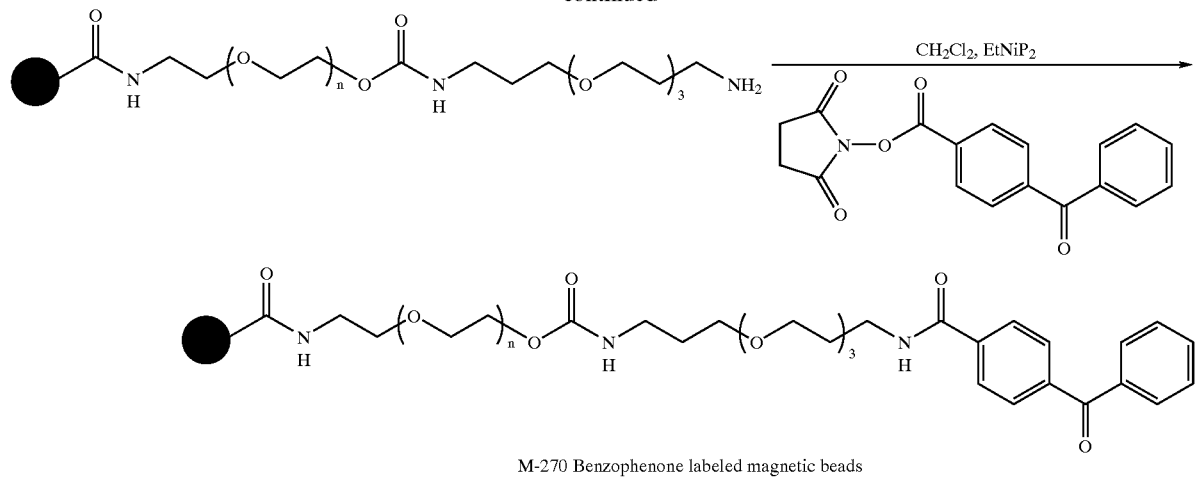
M-270 Benzophenone labeled magnetic beads
Example 8
Scheme for the Synthesis of Benzophenone-labeled Dynal M-450 Beads
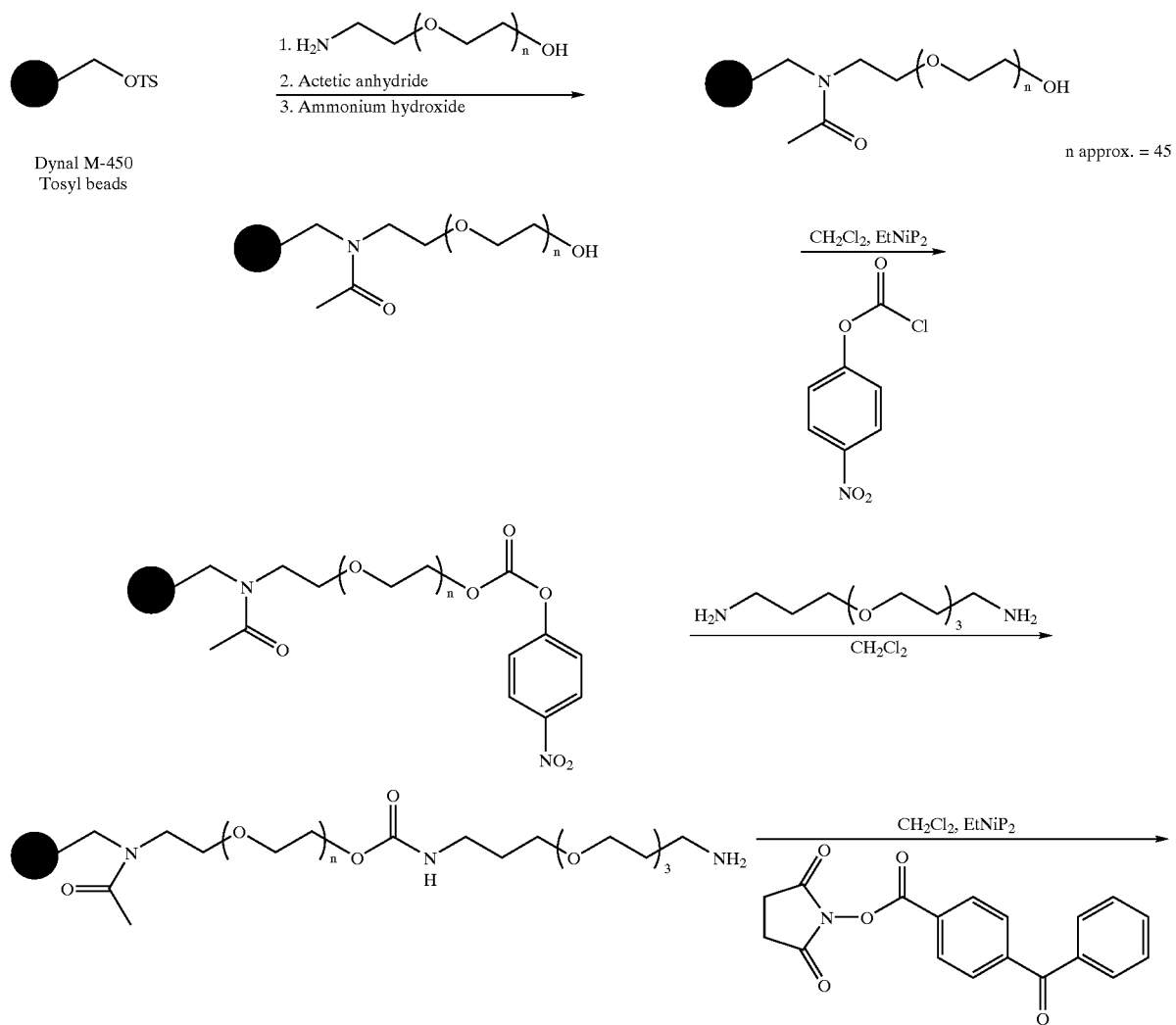

-continued

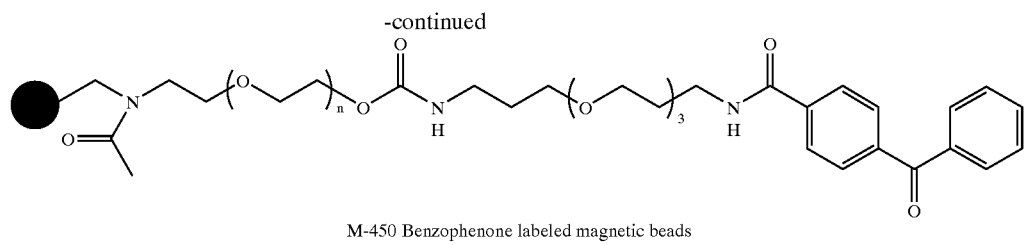

M-450 Benzophenone labeled magnetic beads

Example 9
Scheme for the Attachment of Thrombin to Benzophenone-labeled Beads

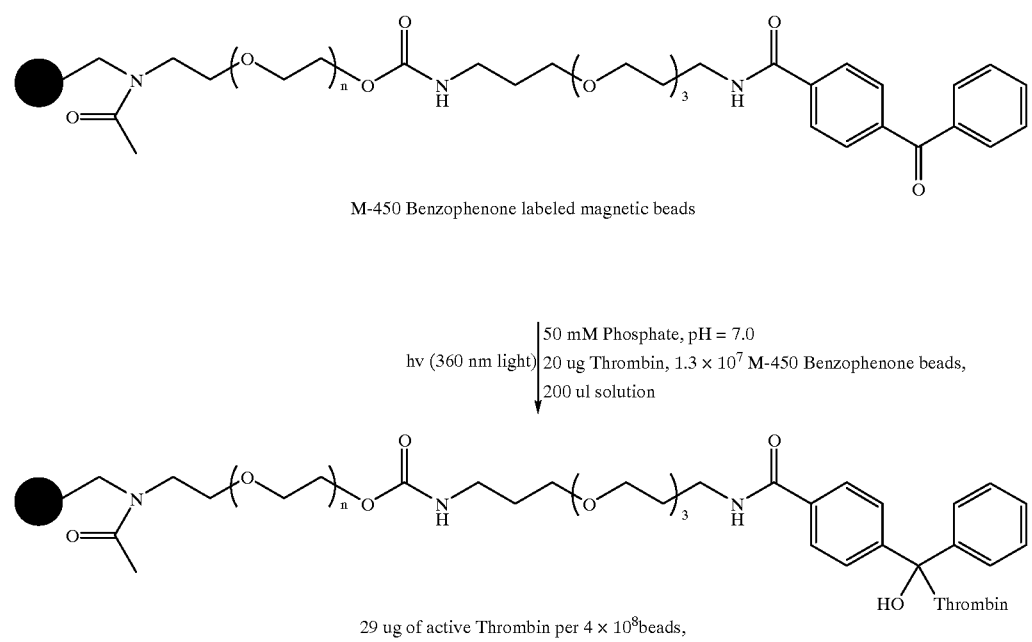

What is claimed is:

1. A method for the identification of a nucleic acid ligand from a candidate mixture of nucleic acids, said nucleic acid ligand being a ligand of a given target, each said nucleic acid in said candidate mixture comprising fixed sequence regions, the method comprising:

a) adding the candidate mixture and the target in a predetermined ratio to a reaction vessel at a work station on a work surface using a cartesian robotic manipulator, wherein nucleic acids having an increased affinity to the target relative to the candidate mixture may be partitioned from the remainder of the candidate mixture;

b) partitioning increased affinity nucleic acids from the remainder of the candidate mixture using said robotic manipulator;

c) PCR-amplifying the increased affinity nucleic acids with primers complementary to said fixed sequence regions to yield a ligand enriched mixture of nucleic acids, wherein the 5' ends of said primers are attached to tail sequences having a lower melting temperature (Tm) than said primers, wherein said PCR-amplification comprises:

i) adding said primers and PCR reagents to the reaction vessel using said robotic manipulator;

ii) thermally-cycling the reaction vessel using a thermal cycler, wherein said thermal cycling comprises performing at a temperature higher than the melting temperature of said tail sequences a denaturation step, a primer annealing step, and a primer extension step, and wherein the amount of amplified product in said reaction vessel is measured during said thermal cycling using a measuring device; and iii) calculating the amount of increased affinity nucleic acids partitioned at step b) using the measured amount of amplified product obtained from said measuring device;

d) adjusting the reaction conditions of steps a)–c) in a predetermined manner in response to the amount of nucleic acid ligand calculated at step c) iii); and e) repeating steps a)–d) at least once, wherein the adjusting performed at step d) controls the stringency of each successive repeat;

wherein said robotic manipulator, said thermocycler, and said measuring device are automatically controlled by a computer during steps a)–e), and wherein said computer automatically calculates the amount of increased affinity product at step c) and automatically adjusts the reaction conditions at step d);

whereby a nucleic acid ligand of said target may be identified.

2. The method of claim 1 wherein said target is attached to a solid support, and wherein step b) is accomplished by automatically partitioning said solid support from said candidate mixture using said robotic manipulator.

3. The method of claim 2 wherein said solid support is a multi-well microtitre plate.

4. The method of claim 3 wherein said plate is comprised of polystyrene.

5. The method of claim 4 wherein said target is attached to said plate by hydrophobic interactions.

6. The method of claim 2 wherein said solid support is a paramagnetic bead and wherein the partitioning of said paramagnetic bead is performed automatically by a magnetic bead separator controlled by said computer.

7. The method of claim 1 wherein each nucleic acid in said candidate mixture of nucleic acid ligands has a tail sequence at both the 5' terminus and the 3' terminus, wherein each tail sequence has a lower melting temperature (Tm) than said fixed sequence regions.

8. The method of claim 1 wherein step c) is performed in the presence of a fluorescent nucleic acid-intercalating dye, said dye undergoing a change in fluorescence intensity upon binding double-stranded DNA, and wherein the amount of amplified product is measured by quantitating a fluorescence signal from said dye.

9. A method for the identification of a nucleic acid ligand from a candidate mixture of nucleic acids, said nucleic acid ligand being a ligand of a given target, each said nucleic acid in said candidate mixture comprising fixed sequence regions, the method comprising:

a) contacting the candidate mixture with the target wherein nucleic acids having an increased affinity to the target relative to the candidate mixture may be partitioned from the remainder of the candidate mixture;

b) partitioning increased affinity nucleic acids from the remainder of the candidate mixture; and c) PCR-amplifying the increased affinity nucleic acids with primers complementary to said fixed sequence regions to yield a ligand enriched mixture of nucleic acids, wherein the 5' ends of said primers are attached to tail sequences having a lower melting temperature (Tm) than said primers, wherein the polymerase chain reaction comprises a denaturation step, a primer annealing step, and a primer extension step, wherein said primer annealing step and said primer extension step are performed at a temperature higher than the melting temperature of said tail sequences;

d) repeating steps a) through c) using the ligand enriched mixture of each successive repeat as many times as required to yield a desired level of increased ligand enrichment;

wherein said candidate mixture comprises the sequence set forth in SEQ. ID. NO:7, and wherein said primers comprise the sequences set forth in SEQ. ID NO: 16 and SEQ. ID. NO:25;

whereby a nucleic acid ligand may be identified.

* * * * *